United States Patent
Müller-Trutwin et al.

(10) Patent No.: US 9,523,687 B2
(45) Date of Patent: Dec. 20, 2016

(54) LEVELS OF CXCL 10/IP-10 FORMS AND SOLUBLE CD26/DPPIV ACTIVITY AS EARLY PREDICTIVE BIOMARKERS FOR HIV/SIV ASSOCIATED MUCOSAL INFLAMMATION AND PROGRESSION TOWARDS AIDS

(71) Applicant: INSTITUT PASTEUR, Paris (FR)

(72) Inventors: Michaela Müller-Trutwin, Paris (FR); Mickaël J. Y. Ploquin, Paris (FR); Matthew Albert, Paris (FR); Yoann Madec, Paris (FR); Cécile Goujard, Paris (FR); Laurence Meyer, Paris (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 14/193,835

(22) Filed: Feb. 28, 2014

(65) Prior Publication Data

US 2015/0247853 A1    Sep. 3, 2015

(51) Int. Cl.
*G01N 33/00* (2006.01)
*G01N 33/569* (2006.01)

(52) U.S. Cl.
CPC ... *G01N 33/56988* (2013.01); *G01N 2333/522* (2013.01); *G01N 2333/70596* (2013.01); *G01N 2800/50* (2013.01); *G01N 2800/52* (2013.01)

(58) Field of Classification Search
CPC ............... C12Q 2600/158; G01N 2333/7158; G01N 2800/52; G01N 33/6863
See application file for complete search history.

(56) References Cited

U.S. PATENT DOCUMENTS

| | | | |
|---|---|---|---|
| 4,935,493 A | 6/1990 | Bachovchin et al. | |
| 5,296,604 A | 3/1994 | Hanko et al. | |
| 5,462,928 A | 10/1995 | Bachovchin et al. | |
| 5,543,396 A | 8/1996 | Powers et al. | |
| 6,100,234 A | 8/2000 | Huber et al. | |
| 8,124,332 B2 * | 2/2012 | Albert .................. | C12Q 1/6883 424/85.1 |

FOREIGN PATENT DOCUMENTS

| | | |
|---|---|---|
| WO | WO 93/10127 A1 | 5/1993 |
| WO | WO 2009/027514 | * 3/2009 |

OTHER PUBLICATIONS

Cohen, J. Promising AIDS Vaccine's Failure Leaves Field Reeling. Science, 2007; 318: 28-29.*
Barouch, D.H. Challenges in the development of an HIV-1 vaccine. Nature, 2008; 455: 613-619.*
Kwong et al. Rational Design of Vaccines to Elicit Broadly Neutralizing Antibodies to HIV-1. Cold Spring Harb. Perspect. Med. 2011;.1:a007278: 1-16.*

(Continued)

*Primary Examiner* — Janet L Andres
*Assistant Examiner* — Stuart W Snyder
(74) *Attorney, Agent, or Firm* — Oblon, McClelland, Maier & Neustadt, L.L.P.

(57) ABSTRACT

The invention provides methods for the identification of patients capable of controlling HIV progression, as well as to the identification of an antagonist form of IP-10 associated to HIV progression control and the uses thereof for improving the immunological response of HIV patients.

8 Claims, 6 Drawing Sheets

(56) References Cited

OTHER PUBLICATIONS

Montaner et al. Multiple drug rescue therapy for HIV-infected individuals with prior virologic failure to multiple regimens. AIDS, 2001; 15:61-69.*

Klein, M. Current progress in the development of human immunodeficiency virus vaccines: research and clinical trials. Vaccine, 2001; 19: 2210-2215.*

Michael W. Adler, et al., "Range and Natural History of Infection", British Medical Journal, vol. 294, (May 2, 1987), pp. 1145-1147.

Ingrid De Meester, et al., "CD26, let it cut or cut it down", Immunology Today, vol. 20, No. 8, (Aug. 1999), pp. 367-375.

K. Augustyns, et al., "The Unique Properties of Dipeptidyl-peptidase IV (DPP IV / CD26) and the Therapeutic Potential of DPP IV Inhibitors", Current Medicinal Chemistry, vol. 6, (1999), pp. 311-327.

D. Michael Evans, "Dipeptidyl peptidase IV inhibitors", IDrugs, vol. 5, No. 6, (2002), pp. 577-585.

Ann E. Weber, "Dipeptidyl Peptidase IV Inhibitors for the Treatment of Diabetes", J. Med. Chem., vol. 47, No. 17, (2004), pp. 4135-4141.

Christopher H.S. McIntosh, et al., "Applications of dipeptidyl peptidase IV inhibitors in diabetes mellitus", The International Journal of Biochemistry & Cell Biology, vol. 38, No. 5-6, (2006), pp. 860-872.

Paul E. Wiedeman, et al., "Dipeptidyl peptidase IV inhibitors for the treatment of impaired glucose tolerance and type 2 diabetes", Current Opinion in Investigational Drugs, vol. 4, No. 4, (2003), pp. 412-420.

Christopher Kornfeld, et al., "Antiinflammatory profiles during primary SIV infection in African green monkeys are associated with protection against AIDS", The Journal of Clinical Investigation, vol. 115, No. 4, (Apr. 2005), pp. 1082-1091.

Mickaël J-Y Ploquin, et al., "Distinct expression profiles of TGF-β1 signaling mediators in pathogenic SIVmac and non-pathogenic SIVagm infections", Retrovirology, vol. 3, No. 37, (2006), 6 pages.

Ousmane M. Diop, et al., "Plasmacytoid Dendritic Cell Dynamics and Alpha Interferon Production during Simian Immunodeficiency Virus Infection with a Nonpathogenic Outcome", Journal of Virology, vol. 82, No. 11, (Jun. 2008), pp. 5145-5152.

Beatrice Jacquelin, et al., "Nonpathogenic SIV infection of African green monkeys induces a strong but rapidly controlled type I IFN response", The Journal of Clinical Investigation, vol. 119, No. 12, (Dec. 2009), pp. 3544-3555.

David Favre, et al., "Critical Loss of the Balance between Th17 and T Regulatory Cell Populations in Pathogenic SIV Infection", Plos Pathogens, vol. 5, No. 2, (Feb. 2009), e1000295, 17 pages.

A-S. Liovat, et al., "IP10 and IL18 plasma levels during acute HIV infection are associated with T cell activation and disease progression", Keystone Symposium on HIV Evolution, Genomics and Pathogenesis, Whistler, Canada 2011, 1 page.

A-S. Liovat, et al. "Acute Plasma Biomarkers of T Cell Activation Set-Point Levels and of Disease Progression in HIV-1 Infection", Plos One, vol. 7, No. 10, (Oct. 2012), e46143, 13 pages.

A-S. Liovat, et al., "Acute pro- and anti-inflammatory plasma biomarkers of T cell activation setpoint levels and disease progression in HIV-1 infection", 6th IAS Conference on HIV Pathogenesis, Treatment and Prevention, TUPE069—Poster Exhibition, (Jul. 17-20, 2011), 1 page.

Lindi Roberts, et al., "Plasma cytokine levels during acute HIV-1 infection predict HIV disease progression", AIDS, vol. 24, No. 6, (Mar. 27, 2010), pp. 819-831.

Yanmei Jiao, et al., "Plasma IP-10 Is Associated with Rapid Disease Progression in Early HIV-1 Infection", Viral Immunology, vol. 25, No. 4, (Aug. 2012), pp. 333-337.

Anupa Kamat, et al., "A Plasma Biomarker Signature of Immune Activation in HIV Patients on Antiretroviral Therapy", Plos One, vol. 7, No. 2, (Feb. 2012), e30881, 11 pages.

Sheila M. Keating, et al., "The effect of HIV infection and HAART on inflammatory biomarkers in a population-based cohort of women", AIDS, vol. 25, No. 15, (2011), pp. 1823-1832.

Cynthia Gay, et al., "Cross-Sectional Detection of Acute HIV Infection: Timing of Transmission, Inflammation and Antiretroviral Therapy", Plos One, vol. 6, No. 5, (May 2011), e19617, 10 pages.

Armanda Casrouge, et al., "Evidence for an antagonist form of the chemokine CXCL10 in patients chronically infected with HCV", The Journal of Clinical Investigation, vol. 121, No. 1, (Jan. 2011), pp. 308-317.

A. Casrouge, et al., "Discrimination of agonist and antagonist forms of CXCL10 in biological samples", Clinical and Experimental Immunology, The Journal of Translational Immunology, vol. 167, No. 1, pp. 137-148.

M. Valle Blazquez, et al., "Selective Decrease of CD26 Expression in T Cells From HIV-1-Infected Individuals" The Journal of Immunology, The American Association of Immunologists, vol. 149, No. 9, (Nov. 1, 1992), 3073-3077.

Andrea De Pasquale, et al. "Dipeptidyl Amino Peptidase IV Cytochemistry in Circulating Lymphocytes from HIV-I-Seropositive Subjects", Acta Haemat, vol. 81, No. 1, (1989), pp. 19-21.

M.-L. Gougeon, et al., "Selective loss of the CD4[+]/CD26[+]T-cell subset during HIV infection", Res. Immunol., vol. 147, No. 1, (1996), pp. 5-8.

G. Vanham, et al., "Decreased Expression of the Memory Marker CD26 on Both CD4[+]and CD8[+]T Lymphocytes of HIV-Infected Subjects", Journal of Acquired Immune Deficiency Syndromes, vol. 6, No. 7, (1993), pp. 749-757.

Daniel Douek, "HIV Disease Progression: Immune Activation, Microbes, and a Leaky Gut", Topics in HIV Medicine, International AIDS Society-USA, vol. 15, No. 4, (2007), pp. 114-117.

\* cited by examiner

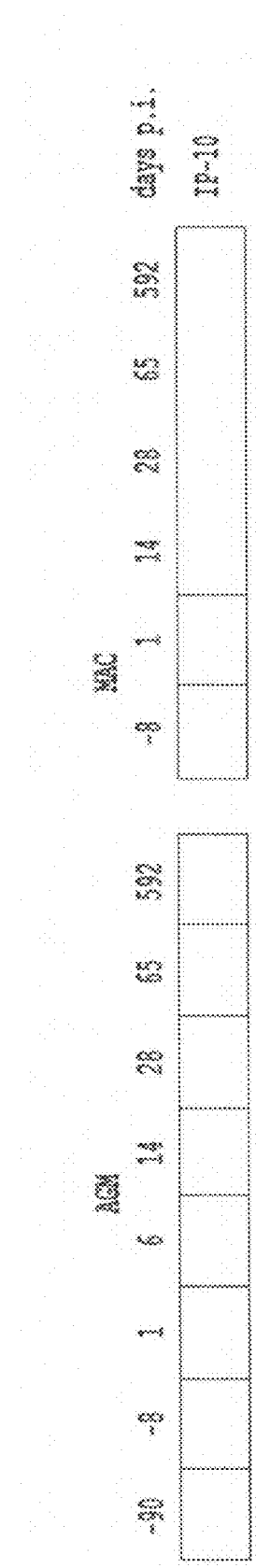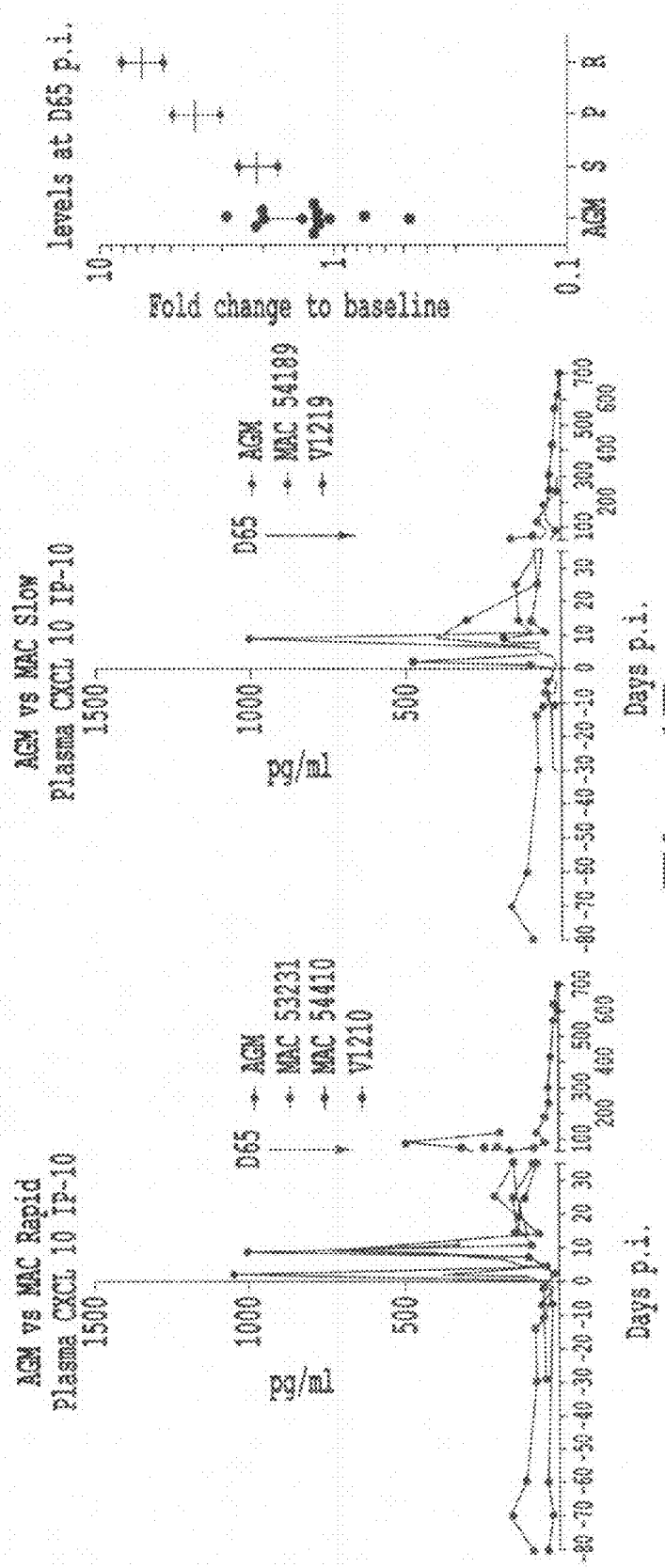
Fig. 1A
Fig. 1B

| | IP-10 p value | Co-marker p value |
|---|---|---|
| IP-10 + CD4 | 0.004 | 0.23 |
| IP-10 + RNA | 0.005 | 0.80 |
| IP-10 + DNA | 0.003 | 0.67 |

Fig. 2

SEQUENCE LISTING

```
<160> NUMBER OF SEQ ID NOS: 4

<210> SEQ ID NO 1
<211> LENGTH: 77
<212> TYPE: PRT
<213> ORGANISM: Homo sapiens
<220> FEATURE:
<221> NAME/KEY: misc_feature
<223> OTHER INFORMATION: IP-10

<400> SEQUENCE: 1

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45
```

```
Gly Glu Lys Arg Cys Leu Asn Pro Glu Ser Lys Ala Ile Lys Asn Leu
        50                  55                  60

Leu Lys Ala Val Ser Lys Glu Met Ser Lys Arg Ser Pro
 65                  70                  75

<210> SEQ ID NO 2
<211> LENGTH: 75
<212> TYPE: PRT
<213> ORGANISM: Homo sapiens
<220> FEATURE:
<221> NAME/KEY: misc_feature
<223> OTHER INFORMATION: sIP-10

<400> SEQUENCE: 2

Leu Ser Arg Thr Val Arg Cys Thr Cys Ile Ser Ile Ser Asn Gln Pro
 1               5                  10                  15

Val Asn Pro Arg Ser Leu Glu Lys Leu Glu Ile Ile Pro Ala Ser Gln
                20                  25                  30

Phe Cys Pro Arg Val Glu Ile Ile Ala Thr Met Lys Lys Lys Gly Glu
            35                  40                  45

Lys Arg Cys Leu Asn Pro Glu Ser Lys Ala Ile Lys Asn Leu Leu Lys
        50                  55                  60

Ala Val Ser Lys Glu Met Ser Lys Arg Ser Pro
 65                  70                  75

<210> SEQ ID NO 3
<211> LENGTH: 766
<212> TYPE: PRT
<213> ORGANISM: Homo sapiens
<220> FEATURE:
<221> NAME/KEY: misc_feature
<223> OTHER INFORMATION: human DPPIV protein (Swissprot database
      Accession No. P27487)

<400> SEQUENCE: 3

Met Lys Thr Pro Trp Lys Val Leu Leu Gly Leu Leu Gly Ala Ala Ala
 1               5                  10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
            35                  40                  45

Leu Lys Asn Thr Tyr Arg Leu Lys Leu Tyr Ser Leu Arg Trp Ile Ser
        50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
```

-continued

```
            180                 185                 190
Ile Ile Tyr Asn Gly Ile Thr Asp Trp Val Tyr Glu Glu Val Phe
        195                 200                 205
Ser Ala Tyr Ser Ala Leu Trp Trp Ser Pro Asn Gly Thr Phe Leu Ala
        210                 215                 220
Tyr Ala Gln Phe Asn Asp Thr Glu Val Pro Leu Ile Glu Tyr Ser Phe
225                 230                 235                 240
Tyr Ser Asp Glu Ser Leu Gln Tyr Pro Lys Thr Val Arg Val Pro Tyr
                245                 250                 255
Pro Lys Ala Gly Ala Val Asn Pro Thr Val Lys Phe Phe Val Val Asn
                260                 265                 270
Thr Asp Ser Leu Ser Ser Val Thr Asn Ala Thr Ser Ile Gln Ile Thr
                275                 280                 285
Ala Pro Ala Ser Met Leu Ile Gly Asp His Tyr Leu Cys Asp Val Thr
                290                 295                 300
Trp Ala Thr Gln Glu Arg Ile Ser Leu Gln Trp Leu Arg Arg Ile Gln
305                 310                 315                 320
Asn Tyr Ser Val Met Asp Ile Cys Asp Tyr Asp Glu Ser Ser Gly Arg
                325                 330                 335
Trp Asn Cys Leu Val Ala Arg Gln His Ile Glu Met Ser Thr Thr Gly
                340                 345                 350
Trp Val Gly Arg Phe Arg Pro Ser Glu Pro His Phe Thr Leu Asp Gly
                355                 360                 365
Asn Ser Phe Tyr Lys Ile Ile Ser Asn Glu Glu Gly Tyr Arg His Ile
                370                 375                 380
Cys Tyr Phe Gln Ile Asp Lys Lys Asp Cys Thr Phe Ile Thr Lys Gly
385                 390                 395                 400
Thr Trp Glu Val Ile Gly Ile Glu Ala Leu Thr Ser Asp Tyr Leu Tyr
                405                 410                 415
Tyr Ile Ser Asn Glu Tyr Lys Gly Met Pro Gly Gly Arg Asn Leu Tyr
                420                 425                 430
Lys Ile Gln Leu Ser Asp Tyr Thr Lys Val Thr Cys Leu Ser Cys Glu
                435                 440                 445
Leu Asn Pro Glu Arg Cys Gln Tyr Tyr Ser Val Ser Phe Ser Lys Glu
                450                 455                 460
Ala Lys Tyr Tyr Gln Leu Arg Cys Ser Gly Pro Gly Leu Pro Leu Tyr
465                 470                 475                 480
Thr Leu His Ser Ser Val Asn Asp Lys Gly Leu Arg Val Leu Glu Asp
                485                 490                 495
Asn Ser Ala Leu Asp Lys Met Leu Gln Asn Val Gln Met Pro Ser Lys
                500                 505                 510
Lys Leu Asp Phe Ile Ile Leu Asn Glu Thr Lys Phe Trp Tyr Gln Met
                515                 520                 525
Ile Leu Pro Pro His Phe Asp Lys Ser Lys Tyr Pro Leu Leu Leu
                530                 535                 540
Asp Val Tyr Ala Gly Pro Cys Ser Gln Lys Ala Asp Thr Val Phe Arg
545                 550                 555                 560
Leu Asn Trp Ala Thr Tyr Leu Ala Ser Thr Glu Asn Ile Ile Val Ala
                565                 570                 575
Ser Phe Asp Gly Arg Gly Ser Gly Tyr Gln Gly Asp Lys Ile Met His
                580                 585                 590
Ala Ile Asn Arg Arg Leu Gly Thr Phe Glu Val Glu Asp Gln Ile Glu
                595                 600                 605
```

```
Ala Ala Arg Gln Phe Ser Lys Met Gly Phe Val Asp Asn Lys Arg Ile
    610             615                 620
Ala Ile Trp Gly Trp Ser Tyr Gly Gly Tyr Val Thr Ser Met Val Leu
625             630                 635                 640
Gly Ser Gly Ser Gly Val Phe Lys Cys Gly Ile Ala Val Ala Pro Val
                645                 650                 655
Ser Arg Trp Glu Tyr Tyr Asp Ser Val Tyr Thr Glu Arg Tyr Met Gly
                660                 665                 670
Leu Pro Thr Pro Glu Asp Asn Leu Asp His Tyr Arg Asn Ser Thr Val
            675                 680                 685
Met Ser Arg Ala Glu Asn Phe Lys Gln Val Glu Tyr Leu Leu Ile His
            690                 695                 700
Gly Thr Ala Asp Asp Asn Val His Phe Gln Gln Ser Ala Gln Ile Ser
705                 710                 715                 720
Lys Ala Leu Val Asp Val Gly Val Asp Phe Gln Ala Met Trp Tyr Thr
                725                 730                 735
Asp Glu Asp His Gly Ile Ala Ser Ser Thr Ala His Gln His Ile Tyr
                740                 745                 750
Thr His Met Ser His Phe Ile Lys Gln Cys Phe Ser Leu Pro
            755                 760                 765

<210> SEQ ID NO 4
<211> LENGTH: 9
<212> TYPE: PRT
<213> ORGANISM: Artificial Sequence
<220> FEATURE:
<223> OTHER INFORMATION: NH2 terminal of the full-length IP-10 protein

<400> SEQUENCE: 4

Val Pro Leu Ser Arg Thr Val Arg Cys
1               5
```

LEVELS OF CXCL 10/IP-10 FORMS AND SOLUBLE CD26/DPPIV ACTIVITY AS EARLY PREDICTIVE BIOMARKERS FOR HIV/SIV ASSOCIATED MUCOSAL INFLAMMATION AND PROGRESSION TOWARDS AIDS

FIELD OF THE INVENTION

The invention relates to the field of immunology and, in particular, to methods for the identification of patients capable of controlling HIV progression, as well as to the identification of an antagonist form of IP-10 associated to HIV progression control and the uses thereof for improving the immunological response of HIV patients.

BACKGROUND OF THE INVENTION

HIV disease is a continuum of progressive damage to the immune system from the time of infection to the manifestation of severe immunologic damage by opportunistic infections, neoplasms, wasting, or low CD4 lymphocyte count that define AIDS. In the absence of antiretroviral therapy, this results in an important immunologic impairment with the consequent appearance of opportunistic infections and, lastly, death. The time it takes to traverse this spectrum varies greatly, ranging from 1 year or less in some persons to a still unknown upper limit in others that has reached nearly 20 years in a few individuals.

Significant advances in antiretroviral therapy of HIV infection have been made since the introduction of zidovudine (AZT) in 1987. Intensive research on HIV led to the development of highly active antiretroviral therapies (HAART). HAART is defined as treatment with at least three active anti-retroviral medications, commonly reverse transcriptase inhibitors and protease inhibitors. These therapies have been extremely successful in controlling the spread of the disease. Indeed, with the advent of HAART, HIV infection is now manageable as a chronic disease in patients who have access to medication and who achieve durable virological suppression.

However, residual chronic inflammation persists in HAART-treated patients and is associated with increased risk of cardiovascular diseases and mortality. Both AIDS and non-AIDS mortality are attributed to chronic inflammation in HIV-infected individuals. No therapeutic strategy exists to reduce this inflammation efficiently. This is in part explained by the fact that the inflammatory pathways involved are not well identified. Chronic immune activation is considered as the major driving force for CD4$^+$ T cell depletion and progression towards AIDS in HIV-infected individuals. HIV-triggered chronic inflammation remains higher even in patients who control viral load (patients under efficient anti-retroviral treatment and HIV controllers in comparison to healthy donors. Current antiretroviral treatments are highly efficient, but fail to abolish residual chronic immune activation.

There is thus an urgent need to understand the factors, which drive this inflammation and to define good surrogate markers for this inflammation.

BRIEF SUMMARY OF THE INVENTION

The present disclosure is related to the discovery that levels of certain biomarkers, including the short form of IP-10 (sIP-10), in the plasma of HIV patients are negative predictors of those patients who will progress towards AIDS.

Accordingly, in one aspect of the invention, a method is provided for assessing the likelihood of a patient to develop AIDS. Generally, the method includes at least the following steps: (1) assaying a biological sample from a patient identified as infected with HIV to determine the level of sIP-10 in the biological sample; and (2) assessing the likelihood that the patient will develop AIDS based on the level of sIP-10.

In another aspect of the invention, a method is provided for prognosing of a patient identified as suffering from HIV infection. Generally, the method includes at least the following steps: (1) determining the level of sIP-10 in a biological sample taken from the patient; and (2) determining the prognosis of the patient based on the level of sIP-10.

In another aspect of the invention, a method is provided for treating HIV infection. Generally, the method includes at least the following steps: (1) obtaining a biological sample from a patient identified as having HIV infection; (2) determining the level of sIP-10 in the biological sample; and (3) selecting a drug therapy based on the level of sIP-10 in the sample.

More precisely, the present disclosure is related to the discovery that the relative levels of sIP-10 are negative predictors of those patients who will progress towards AIDS.

Accordingly, in one aspect of the invention, a method is provided for assessing the likelihood of a patient to develop AIDS. Generally, the method includes at least the following steps: (1) assaying a biological sample from a patient identified as infected with HIV to determine the level of sIP-10 in the biological sample; (2) determining the ratio of sIP-10 to total IP-10, and (3) assessing the likelihood that the patient will develop AIDS based on the ratio of sIP-10 to total IP-10.

In another aspect of the invention, a method is provided for prognosing of a patient identified as suffering from HIV infection. Generally, the method includes at least the following steps: (1) determining the level of sIP-10 in a biological sample taken from the patient; (2) determining the ratio of sIP-10 to total IP-10 in said biological sample, and (3) determining the prognosis of the patient based on the ratio of sIP-10 to total IP-10.

In another aspect of the invention, a method is provided for treating HIV infection. Generally, the method includes at least the following steps: (1) obtaining a biological sample from a patient identified as having HIV infection; (2) determining the level of sIP-10 in the biological sample; (3) determining the ratio of sIP-10 to total IP-10 in the biological sample, and (4) selecting a drug therapy based on the ratio of sIP-10 to total IP-10 in the sample.

The present disclosure is also related to the discovery that the enzymatic activities of certain biomarkers, including the dipeptidylpeptidase IV enzyme (DPPIV), in the plasma of HCV patients are negative predictors of those patients who will progress towards AIDS.

Accordingly, in one aspect of the invention, a method is provided for assessing the likelihood of a patient to develop AIDS. Generally, the method includes at least the following steps: (1) assaying a biological sample from a patient identified as infected with HIV to determine the activity of DPPIV in the biological sample; and (2) assessing the likelihood that the patient will develop AIDS based on the activity of DPPIV.

In another aspect of the invention, a method is provided for prognosing of a patient identified as suffering from HIV infection. Generally, the method includes at least the following steps: (1) determining the activity of DPPIV in a biological sample taken from the patient; and (2) determining the prognosis of the patient based on the activity of DPPIV.

In another aspect of the invention, a method is provided for treating HIV infection. Generally, the method includes at least the following steps: (1) obtaining a biological sample from a patient identified as having HIV infection; (2) determining the activity of DPPIV in the biological sample; and (3) selecting a drug therapy based on the activity of DPPIV in the sample.

All methods and materials similar or equivalent to those described herein can be used in the practice or testing of the present invention, with suitable methods and materials being described herein. The practice of the invention employs, unless other otherwise indicated, conventional techniques or protein chemistry, molecular virology, microbiology, recombinant DNA technology, and pharmacology, which are within the skill of the art. Such techniques are explained fully in the literature (see e.g., Ausubel et al., Short Protocols in Molecular Biology, Current Protocols; 5th Ed., 2002; Remington's Pharmaceutical Sciences, 17th ed., Mack Publishing Co., Easton, Pa., 1985; and Sambrook et al., Molecular Cloning: A Laboratory Manual, Cold Spring Harbor Laboratory Press; 3rd Ed., 2001). The nomenclatures used in connection with, and the laboratory procedures and techniques of, molecular and cellular biology, protein biochemistry, enzymology and medicinal and pharmaceutical chemistry described herein are those well-known and commonly used in the art. All publications, patent applications, patents, and other references mentioned herein are incorporated by reference in their entirety. Further, the materials, methods, and examples are illustrative only and are not intended to be limiting, unless otherwise specified.

Other features and advantages of the invention will be apparent from the following detailed description, and from the claims.

BRIEF DESCRIPTION OF THE DRAWINGS

FIG. 1: Controlled CXCL10/IP-10 expression in non-pathogenic SIV infection. A. IP-10 gene expression levels in enriched lymph node CD4+ cells are shown here as heatmap. Gene expression levels were assessed using microarrays at different time points before and after SIVagm and SIVmac infection in AGM and MAC, respectively. B. IP-10 expression levels in plasma before and after SIVagm and SIVmac infection are represented here. Levels were quantified using a commercial ELISA (R&D) as described in (Liovat et al., *PLoS One*, 7(10): e46143, 2012). Median from 12 AGM is displayed along with levels obtained in 3 MAC with a rapid disease progression profile or with 2 MAC with a slow disease progression profile. In addition data are shown also as a fold change of levels measured at day 65 p.i. against median of values assessed before infection for each animal. S=MAC slow progressor, P=MAC progressor and R=MAC rapid progressor.

FIG. 2: IP-10 robustness of prediction for rapid disease progression. Multivariate regression analysis. Only IP-10 was significant in the multivariate analysis for prediction of rapid disease progression, while CD4+ T cell counts, plasma viral RNA and cellular viral DNA levels were not.

DETAILED DESCRIPTION OF THE INVENTION

Definitions

Figure 3:
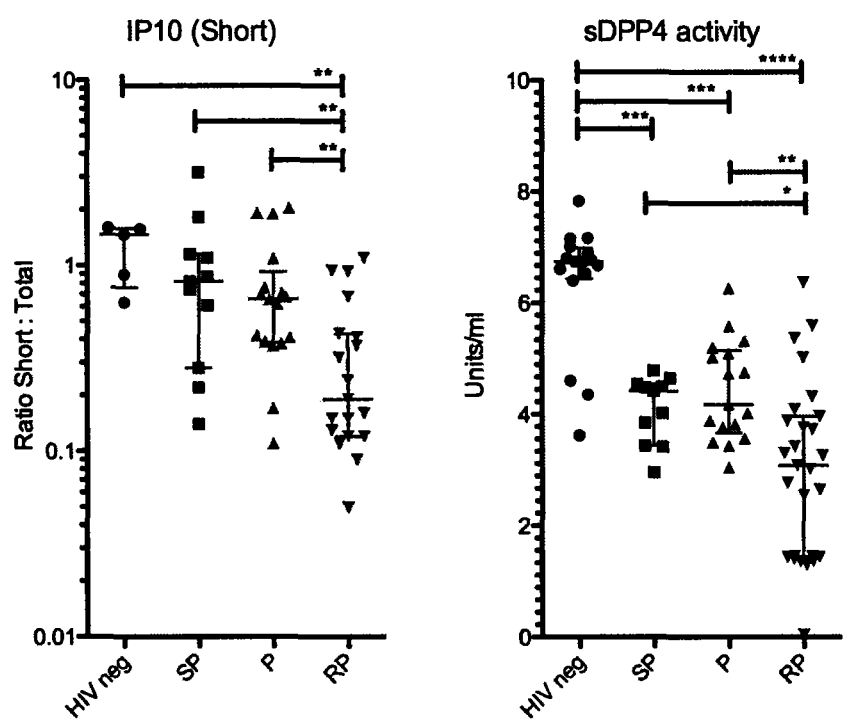
FIG. 3: Decreased levels of plasma IP-10 antagonist form and sDPPIV-like activity during acute infection in HIV-1 infected individuals progressing rapidly to disease. Frozen plasmas collected on EDTA were obtained from 134 HIV patients during primary infection (Fiebig stage III-IV) of the ANRS Primo Cohort Co6, and described in (Liovat et al., *PLoS One,* 7(10): e46143, 2012). Plasma IP-10 antagonist form (short) is presented as a ratio short (antagonist form): total IP-10. Total IP10 concentrations were previously measured (Liovat et al., *PLoS One,* 7(10): e46143, 2012). We also monitored the bioactive sDPPIV titers in plasma, determined with a luminescence-based assay (Promega). Mann-Whitney test was used to compare groups of patients. Preliminary data from 53 patients are shown: HIV neg (n=5-16), slow progressors (SP, n=11), progressors (P, n=17), rapid progressors (RP, n=25).

Unless specifically defined, all technical and scientific terms used herein have the same meaning as commonly understood by a skill artisan in chemistry, biochemistry, cellular biology, molecular biology, and medical sciences.

The term "AIDS", as used herein, refers to the symptomatic phase of HIV infection, and includes both Acquired Immune Deficiency Syndrome (commonly known as AIDS) and "ARC," or AIDS-Related Complex. See Adler M, et al, Brit. Med. J. 1987; 294: 1145-1147. The immunological and clinical manifestations of AIDS are known in the art and include, for example, opportunistic infections and cancers resulting from immune deficiency.

As used herein, "T-cell" refers to a group of white blood cells known as T-lymphocytes that play a central role in cell-mediated immunity. There are several subsets of T cells, each with a distinct function (i.e. helper, memory, regulatory, natural killer).

The term "$CD4^+$ T cells", as used herein, refers to a type of T cells that expresses the CD4 marker. Said $CD4^+$ T cells are generally treated as having a pre-defined role as helper T cells within the immune system. "CD4", as used herein, refers to a cluster of differentiation 4, a glycoprotein expressed on the surface of T helper cells, monocytes, macrophages, and dendritic cells. CD4 is a co-receptor that assists the T cell receptor (TCR) with an antigen-presenting cell. Using its portion that resides inside the T cell, CD4 amplifies the signal generated by the TCR by recruiting an enzyme, known as the tyrosine kinase lck, which is essential for activating many molecules involved in the signaling cascade of an activated T cell.

The term "CD8+ T cells", as used herein, refers to a type of T cell that expresses the CD8 marker. "CD8", as used herein, refers to cluster of differentiation 8, a transmembrane glycoprotein that serves as a co-receptor for the T cell receptor (TCR) expressed in the cytotoxic T cells implicated in the rejection of transplants and the destruction of tumor and virally infected cells.

As used herein, "T-cell function" means any activities which are inherent to a T-cell. T-cell function means any one of cytokine secretion, (for example, IL-2), proliferation or survival.

As used herein, "T-cell survival" means, the ability of a T-cell to persist in a host organism.

As used herein, "proliferation" refers to a process by which a cell undergoes mitosis, or increases in number, size or content.

The term "controller", as used herein, refers to a HIV infected subject that exhibits a decrease in HIV viral load after infection and that maintains said decreased viral load levels over time. A "controller" also refers to an HIV-1 infected subject who remains asymptomatic with normal CD4+ T-cell counts and low or undetectable plasma viral loads despite having never been treated with antiretroviral medications. HIV controllers are capable of maintaining very low viral load levels, for example, plasma HIV R A levels <2000 copies/mL in the absence of antiretroviral therapy, measured three times over a period spanning at least 12 months. The features of controllers as defined by the HIV Controller Consortium are: i) to maintain HIV RNA levels below 2000 copies/mL, ii) no antiretroviral therapy for 1 year or longer and iii) episodes of viremia are acceptable as long as they represent the minority of all available determinations.

The term "decreased", as used herein, refers to the level of a HIV disease prognosis marker, e.g. sIP-10, of a subject at least 1-fold (e.g. 1, 2, 3, 4, 5, 10, 20, 30, 40, 50, 60, 70, 80, 90, 100, 1000, 10,000-fold or more) lower than its reference value. "Decreased", as it refers to the level of a HIV disease prognosis marker, e.g. sIP-10, of a subject, signifies also at least 5% lower (e.g. 5%, 6%, 7%, 8%, 9%, 10%, 15%, 20%, 25%, 30%, 35%, 40%, 45%, 50%, 55%, 60%, 65%, 70%, 75%, 80%, 85%, 90%), 95%), 99%), or 100%) than the level in the reference sample or with respect to the reference value for said prognosis marker.

As used herein, "diagnosis" or "identifying a subject having" refers to a process of determining if an individual is afflicted with a disease or ailment (e.g., HIV). HIV is diagnosed for example by detecting either the presence of an HIV polypeptide, HIV nucleic acid, or a marker associated with HIV.

The term "HIV", as used herein, include HIV-1 and HIV-2 and SIV. "HIV-1" means the human immunodeficiency virus type-1. HIV-1 includes, but is not limited to, extracellular virus particles and the forms of HIV-1 associated with HIV-1 infected cells. HIV-1 is known to comprise at least ten subtypes (A1, A2, A3, A4, B, C, D, E, PL F2, G, H, J and K). See Taylor B, et al, MEJM 2008; 359(18): 1965-1966. Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India, and China, areas where the incidence of new HIV infections is high, HIV-1 subtype B accounts for only a small minority of infections, and subtype HIV-1 C appears to be the most common infecting subtype. "HIV-2" means the human immunodeficiency virus type-2. HIV-2 includes, but is not limited to, extracellular virus particles and the forms of HIV-2 associated with HIV-2 infected cells. HIV-2 is known to include at least five subtypes (A, B, C, D, and E). The term "SIV" refers to simian immunodeficiency virus which is an HIV-like virus that infects monkeys, chimpanzees, and other nonhuman primates. SIV includes, but is not limited to, extracellular virus particles and the forms of SIV associated with SIV infected cells.

As used herein, a "HIV disease" encompasses basically all the physiological conditions that are undergone by an individual who has been infected by a HIV virus, starting from the time of the virus infection event until the date of the individual's death, irrespective of whether the individual's death is a direct or indirect consequence of the virus infection event. It is recalled that the infection of an individual with a HIV virus causes a chronic disease state that progressively causes a reduction of the effectiveness of the immune system and leaves the HIV-infected individuals susceptible to opportunistic infections and tumors. Thus, a HIV disease encompasses the primary infection (or acute infection) time period, the seroconversion time period, the asymptomatic stage time period, the early- and medium-stage of HIV symptomatic disease, as well as the late stage of HIV-1 disease (also called AIDS).

As used herein, "identifying" as it refers to a subject that has a condition refers to the process of assessing a subject and determining that the subject has a condition, for example, is infected with HIV.

The term "increased", as used herein, refers to the level of a HIV disease prognosis marker, e.g. sIP-10, of a subject at least 1-fold (e.g. 1, 2, 3, 4, 5, 10, 20, 30, 40, 50, 60, 70, 80, 90, 100, 1000, 10,000-fold or more) greater than its reference value. "Increased", as it refers to the level of a HIV disease prognosis marker, e.g. sIP-10, of a subject, signifies also at least 5% greater (e.g. 5%, 6%, 7%, 8%, 9%, 10%, 15%, 20%, 25%, 30%, 35%, 40%, 45%, 50%, 55%, 60%, 65%, 70%, 75%, 80%, 85%, 90%), 95%), 99%), or 100%) than the level in the reference sample or with respect to the reference value for said prognosis marker.

As intended herein, the "level" of a HIV disease prognosis marker, e.g. sIP-10, consists of a quantitative value of the said prognosis marker in a sample, e.g. in a sample collected from an HIV-infected patient. In some embodiments, the said quantitative value does not consist of an absolute value that is actually measured, but rather consists of a final value resulting from the taking into consideration of a signal to noise ratio occurring with the assay format used, and/or the taking into consideration of calibration reference values that are used to increase reproducibility of the measures of the level of a HIV disease marker, from assay-to-assay. In some embodiments, the "level" of a HIV disease prognosis marker, e.g. sIP-10, is expressed as arbitrary units, since what is important is that the same kind of arbitrary units are compared (i) from assay-to-assay, or (ii) from one HIV-infected patient to others, or (iii) from assays performed at distinct time periods for the same patient, or (iv) between the HIV prognosis marker level measured in a patients sample and a predetermined reference value (which may also be termed a "cut-off" value herein).

As used herein, "monitoring disease progression" refers to a process of determining the severity or stage of a disease in an individual afflicted with the disease or ailment (e.g., HIV).

As used herein, "prognosis" refers to a process of predicting the probable course and outcome of a disease in an individual afflicted with a disease or ailment (e.g., HIV), or the likelihood of recovery of an individual from a disease (e.g., HIV).

The term "reference value", as used herein, refers to the expression level of a HIV disease prognosis marker under consideration (e.g. sIP-10) in a reference sample. A "reference sample", as used herein, means a sample obtained from subjects, preferably two or more subjects, known to be free of the disease or, alternatively, from the general population. The suitable reference expression levels of HIV disease prognosis marker can be determined by measuring the expression levels of said HIV disease prognosis marker in several suitable subjects, and such reference levels can be adjusted to specific subject populations. The reference value or reference level can be an absolute value; a relative value; a value that has an upper or a lower limit; a range of values; an average value; a median value, a mean value, or a value as compared to a particular control or baseline value. A reference value can be based on an individual sample value such as, for example, a value obtained from a sample from the subject being tested, but at an earlier point in time. The reference value can be based on a large number of samples, such as from population of subjects of the chronological age matched group, or based on a pool of samples including or excluding the sample to be tested.

As used herein, the term "biological sample" or "sample" refers to a whole organism or a subset of its tissues, cells or component parts (e.g. blood vessel, including artery, vein and capillary, body fluids, including but not limited to blood, serum, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, "selecting" refers to the process of determining that an identified subject will receive an agent to treat the occurrence of a condition (e.g., HIV). Selecting can be based on an individual's susceptibility to a particular disease or condition due to, for example, family history, lifestyle, age, ethnicity, or other factors.

A "subject" which may be subjected to the methodology described herein may be any of mammalian animals including human, dog, cat, cattle, goat, pig, swine, sheep and monkey. A human subject can be known as a patient. In one embodiment, "subject" or "subject in need" refers to a mammal that is infected with HIV or is suspected of being infected with HIV or has been diagnosed with HIV infection. As used herein, an "HIV infected subject" refers to a mammal that is infected with HIV or has been diagnosed with HIV infection. A "control subject" refers to a mammal that is not infected with HIV, and is not suspected of being diagnosed with HIV.

As used herein, the terms "treat," treating," "treatment," and the like refer to reducing or ameliorating the symptoms of a disorder (e.g., HIV infection) and/or symptoms associated therewith. It will be appreciated that, although not precluded, treating a disorder or condition does not require that the disorder, condition or symptoms associated therewith be completely eliminated.

As used herein "treating" a disease in a subject or "treating" a subject having a disease refers to subjecting the subject to a pharmaceutical treatment, e.g., the administration of a drug, such that the extent of the disease is decreased or prevented. For example, treating results in the reduction of at least one sign or symptom of the disease or condition. Treatment includes (but is not limited to) administration of a composition, such as a pharmaceutical composition, and may be performed either prophylactically, or subsequent to the initiation of a pathologic event. Treatment can require administration of an agent and/or treatment more than once.

Methods for Prognosing an HIV Disease

IP-10 is a CXC chemokine (NP_001556) which functions to recruit activated and memory lymphocytes to sites of inflammation. The secreted bioactive form (after cleavage of the signal peptide) is a polypeptide of 77 residues (positions 22-98 of NP_001556; SEQ ID NO: 1), herein designated IP-10, which binds the CXCR3 receptor. IP-10 also exists in a truncated form, herein referred to as "short IP-10" or "sIP-10", which is obtained by the removal of the two N-terminal amino acids of the secreted bioactive form (amino acids 24-98 of NP_001556; SEQ ID NO: 2).

In contrast to native IP-10, sIP-10 is endowed with antagonist properties and repels activated and memory lymphocytes from sites of inflammation.

IP-10 has previously been identified as a negative indicator for chronic HCV patients receiving the IFN/ribavirin treatment, i.e. high levels of plasma IP-10 are predictive of the failure to respond to this therapy. These elevated IP-10 levels are mainly in the short antagonist form, preventing trafficking of CXCR3$^+$ lymphocytes capable to control HCV replication, to the liver, thus diminishing HCV control.

The present application discloses sIP-10 as a clinically important negative predictive marker for likelihood to progress rapidly towards AIDS. The present inventors have found that, surprisingly, sIP-10 antagonist levels are dramatically reduced upon HIV infection. Moreover, they were reduced to a higher level in the rapid progressors than in comparison to slow progressors. Indeed, the inventors have shown that sIP-10 is a strong negative predictor of rapid disease progression. Thus, whereas good prognosis is associated with low levels of sIP-10 during HCV infection (Liovat et al., *PLoS One*, 7(10): e46143, 2012), it is correlated with high sIP-10 levels in the case of HIV infection, which was unexpected.

This represents an important and medically useful discovery. This discovery enables the discrimination of patients, prior to treatment, into a group of patients that is likely not to develop clinical AIDS symptoms and a group of patients that will spontaneously progress towards AIDS and will thus require specific and targeted therapeutic treatment. Determining that a patient is likely to remain asymptomatic may save them from expensive treatment with significant side effects. This diagnostic tool may also assist physicians in identifying patients who are likely to progress to AIDS and thus may suggest those patients require earlier or more aggressive treatment.

In a first aspect, the present invention relates to a method of determining the likelihood that a subject identified as being infected with HIV will develop AIDS, said method comprising the steps of:
 a) measuring the sIP-10 level in a sample of the said subject; and
 b) determining the likelihood that said subject will develop AIDS based on the level of step a).

As shown herein, a negative correlation has been surprisingly found by the inventors between the levels of sIP-10 and the likelihood that a patient will progress towards AIDS. The lower the sIP-10 levels, the higher the likelihood that the patient will develop AIDS clinical symptoms.

In an embodiment of the present invention, the said method comprises a prior step of obtaining a biological sample from the said subject.

The present invention also provides a method for prognosing an HIV disease in a subject identified as being infected with HIV, said method comprising the steps of:
 a) measuring the sIP-10 level in a sample of the said subject; and
 b) prognosing the said disease based on the level of step a).

In an embodiment of the present invention, the method for prognosing an HIV disease in a subject infected with an HIV virus includes a prior step of obtaining a biological sample from the said subject.

As explained above, sIP-10 competes with IP-10 for CXCR3 and has antagonistic properties. It is thus informative to express the levels of sIP-10 as a ratio of sIP-10 versus total IP-10, instead of as raw values of sIP-10 concentrations. As used herein, "total IP-10" refers to all the IP-10 isoforms. In other words the total IP-10 in a sample refers to all the IP-10(22-98) and sIP-10(24-98) molecules present in the sample.

In fact, not only is SIP-10 a negative predictor of a rapid progression of an HIV disease, the inventors have shown that the ratio of sIP-10 to total IP-10 was decreased during acute HIV infection in rapid progressors compared to the other HIV-infected patients and compared to healthy subjects.

Therefore, in a preferred embodiment, the method of the invention comprises a further step of measuring the total IP-10 level in the sample. According to another preferred embodiment, the method of the invention comprises a further step of calculating the ratio of sIP-10 to total IP-10. According to a further preferred embodiment, the method of the invention comprises the steps of:

a) measuring the sIP-10 level in a biological sample of a subject identified as being infected with HIV;
 b) measuring the total IP-10 level in said sample of the said subject;
 c) calculating the ratio of sIP-10 to total IP-10; and
 d) prognosing the said disease based on the ratio of step c).

According to a further preferred embodiment, the method of the invention comprises the steps of:
 a) obtaining a biological sample from a subject identified as being infected with HIV;
 b) measuring the sIP-10 level in said sample of the said subject;
 c) measuring the total IP-10 level in said sample of the said subject;
 d) calculating the ratio of sIP-10 to total IP-10; and
 e) prognosing the said disease based on the ratio of step d).

In an embodiment of the method of the invention, the level of sIP-10 or the ratio of sIP-10 to total IP-10 is compared to a reference value. The reference value corresponds for example to the value of the said level or the said ratio in a healthy subject. According to the present invention, a decreased level or ratio is indicative of a bad prognosis, i.e. the subject presents a high likelihood of progressing rapidly towards AIDS. In other words, the said subject has a low likelihood of a long term survival. On the other hand, an increased or a stable level or ratio is indicative of a good prognosis. In this case, the subject displays a low likelihood of progressing rapidly towards AIDS. In other words, the said subject has a high likelihood of a long term survival.

HIV Infected Subjects

Following infection with HIV-1, the rate of clinical disease progression varies between individuals. Factors such as host susceptibility, genetics and immune function, health care and co-infections as well as viral genetic variability [may affect the rate of progression to the point of needing to take medication in order not to develop AIDS. It is thus important to be capable of identifying those who show a higher risk of progressing rapidly towards AIDS.

HIV disease staging and classification systems are critical tools providing clinicians and patients essential information for clinical management. The CDC disease staging system assesses the severity of the HIV disease by $CD4^+$ T lymphocyte cell (CD4) counts and by the presence of specific HIV-related conditions. This system describes the infection in three stages:
 Stage 1: T cell counts ≥500 cells/μl and no AIDS defining conditions;
 Stage 2: T cell counts 200 to 500 cells/μl and no AIDS defining conditions; and
 Stage 3: T cell counts ≤200 cells/μl or AIDS defining conditions.

Thus in an embodiment of the method of the invention, the subject is selected in the group of subjects having T cell counts of less than 200 cells/μL, comprised between 200 and 500 cells/μL, and above 500 cells/μL. In another embodiment of the method of the invention, the subject has T cell counts of less than 200 cells/μL. In another embodiment of the method of the invention, the subject has T cell counts comprised between 200 and 500 cells/μL. In another embodiment of the method of the invention, the subject has T cell counts above 500 cells/μL.

According to the CDC staging system, the definition of AI DS includes all HIV-infected individuals with CD4 counts of less than 200 cells/μL, or a CD4 percentage (over all lymphocytes) of less than 14%, as well as those with certain HIV-related conditions and symptoms. Furthermore, the CDC staging system classifies as eligible for antiretroviral therapy subjects with $CD4^+$ T-lymphocyte counts of less than 500 cells/μL. Yet, some persons having T cell counts above 500 cells/μL are rapid progressors who will advance towards AIDS in the next few months. Those people may also benefit from antiretroviral therapy. It would thus be beneficial to be capable of identifying those subjects which still have T cell counts above 500 cells/μL but have a high risk of developing AIDS in the near future.

Thus in another embodiment, the method of the invention relates to a method for determining the likelihood that a subject identified as being infected with HIV and having T cell counts above 500 cells/μL will develop AIDS, said method comprising the steps of:
 a) measuring the sIP-10 level in a sample of the said subject; and
 b) determining the said likelihood based on the level of step a).

In another aspect of the present invention, a method is provided for determining the likelihood that a subject identified as being infected with HIV and having T cell counts above 500 cells/μL will develop AIDS. Generally, the method includes at least the following steps:
 a) obtaining a biological sample from a subject identified as being infected with HIV and having T cell counts above 500 cells/μL;
 b) measuring the sIP-10 level in said sample of the said subject; and
 c) determining the said likelihood based on the level of step b).

In another embodiment, the method of the invention relates to a method of prognosing an HIV disease in a subject identified as being infected with HIV and having T cell counts above 500 cells/μL, said method comprising the steps of:
 a) measuring the sIP-10 level in a sample of the said subject; and
 b) prognosing the said disease based on the level of step a).

In another aspect of the present invention, a method is provided for prognosing an HIV disease in a subject infected with an HIV virus and having T cell counts above 500 cells/μL. Generally, the method includes at least the following steps:
 a) obtaining a biological sample from a subject identified as being infected with HIV and having T cell counts above 500 cells/μL;
 b) measuring the sIP-10 level in said sample of the said subject; and
 c) prognosing the said disease based on the level of step b).

In a preferred embodiment, the method of the invention comprises a further step of measuring the total IP-10 level in the sample. According to another preferred embodiment, the method of the invention comprises a further step of calculating the ratio of sIP-10 to total IP-10. According to a further preferred embodiment, the method of the invention comprises the steps of:
 a) measuring the sIP-10 level in a biological sample from a subject identified as being infected with HIV and having T cell counts above 500 cells/μL;
 b) measuring the total IP-10 level in said sample of the said subject;
 c) calculating the ratio of sIP-10 to total IP-10; and
 d) prognosing the said disease based on the ratio of step c).

According to a further preferred embodiment, the method of the invention comprises the steps of:
 a) obtaining a biological sample from a subject identified as being infected with HIV and having T cell counts above 500 cells/μL;
 b) measuring the sIP-10 level in said sample of the said subject;
 c) measuring the total IP-10 level in said sample of the said subject;
 d) calculating the ratio of sIP-10 to total IP-10; and
 e) prognosing the said disease based on the ratio of step d).

In an embodiment of the method of the invention, the level of sIP-10 or the ratio of sIP-10 to total IP-10 is compared to a reference value. The reference value corresponds for example to the value of the said level or the said ratio in a healthy subject. According to the present invention, a decreased level or ratio is indicative of a bad prognosis, i.e. the subject presents a high likelihood of progressing rapidly towards AIDS. In other words, the said subject has a low likelihood of a long term survival. On the other hand, an increased or a stable level or ratio is indicative of a good prognosis. In this case, the subject displays a low likelihood of progressing rapidly towards AIDS. In other words, the said subject has a high likelihood of a long term survival.

Human dipeptidyl peptidase IV (DPPIV), which is also known as CD26, is a 110 kDa cell surface molecule. The amino acid sequence of human DPPIV protein comprises 766 amino acids and is shown in SEQ ID NO: 3 (Swissprot database Accession No. P27487). It contains intrinsic dipeptidyl peptidase IV activity which selectively removes N-terminal dipeptide from peptides with proline or alanine in the third amino acid position. It interacts with various extracellular molecules and is also involved in intracellular signal transduction cascades. The multifunctional activities of human DPPIV are dependent on cell type and intracellular or extracellular conditions that influence its role as a proteolytic enzyme, cell surface receptor, co-stimulatory interacting protein and signal transduction mediator. Human DPPIV has a short cytoplasmatic domain from amino acid position 1 to 6, a transmembrane region from amino acid position 7 to 28, and an extracellular domain from amino acid position 29 to 766 with intrinsic dipeptidyl peptidase IV (DPPIV) activity.

It has been shown in the literature that IP-10 is cleaved by DPPIV, resulting in the generation of a short form of IP-10 (sIP-10) that acts as an antagonist of CXCR3 (De Meester et al, 1999, *Immunol Today*, 20(8): 367-375).

The inventors have shown that plasma DPPIV activity is reduced during acute infection in those HIV-infected patients who subsequently progressed more rapidly than the other patients towards AIDS, just like the level of sIP-10. In other words, the activity of DPPIV can be used as a convenient proxy for the level of SIP-10.

The present invention thus also relates to a method of determining the likelihood that a subject identified as being infected with HIV will develop AIDS, said method comprising the steps of:
 a) measuring the DPPIV activity in a sample of the said subject; and
 b) determining the likelihood that said subject will develop AIDS based on the level of step a).

In an embodiment of the present invention, the said method comprises a prior step of obtaining a biological sample from the said subject.

The present invention also provides a method for prognosing an HIV disease in a subject identified as being infected with HIV, said method comprising the steps of:
a) measuring the DPPIV activity in a sample of the said subject; and
b) prognosing the said disease based on the level of step a).

In an embodiment of the present invention, the method for prognosing an HIV disease in a subject infected with an HIV virus includes a prior step of obtaining a biological sample from the said subject.

In an embodiment of the method of the invention, the DPPIV activity is compared to a reference value. The reference value corresponds for example to the value of the said activity in a healthy subject. According to the present invention, a decreased activity is indicative of a bad prognosis, i.e. the subject presents a high likelihood of progressing rapidly towards AIDS. In other words, the said subject has a low likelihood of a long term survival. On the other hand, an increased or a stable activity is indicative of a good prognosis. In this case, the subject displays a low likelihood of progressing rapidly towards AIDS. In other words, the said subject has a high likelihood of a long term survival.

In another aspect, the method of the invention relates to a method of prognosing an HIV disease in a subject identified as being infected with HIV and having T cell counts above 500 cells/μL, said method comprising the steps of:
a) measuring the DPPIV activity in a sample of the said subject; and
b) prognosing the said disease based on the activity of step a).

In an embodiment of the present invention, the said method comprises a prior step of obtaining a biological sample from the said subject.

In an embodiment of the method of the invention, the activity of DPPIV is compared to a reference value. The reference value corresponds for example to the value of the said activity in a healthy subject. According to the present invention, a decreased activity is indicative of a bad prognosis, i.e. the subject presents a high likelihood of progressing rapidly towards AIDS. In other words, the said subject has a low likelihood of a long term survival. On the other hand, an increased or a stable activity is indicative of a good prognosis. In this case, the subject displays a low likelihood of progressing rapidly towards AIDS. In other words, the said subject has a high likelihood of a long term survival.

For the methods herein, the biological sample is preferably a sample from blood, plasma, lymph, bone marrow fluid, pleural fluid, peritoneal fluid, spinal fluid, abdominal fluid, pancreatic fluid, cerebrospinal fluid, brain fluid, ascites, urine, saliva, bronchial lavage, bile, sweat, tears, ear flow, sputum, semen, vaginal flow, milk, amniotic fluid, or secretions of respiratory, intestinal or genitourinary tract. Exemplary of such samples, is a peripheral blood sample, and a body fluid sample that contains dissociated bone marrow cells from a bone marrow biopsy. The volume of sample is any that is convenient for testing, such as at least about 0.01 mL to about 50 mL or 100 ml.

The preparation and/or isolation of proteinaceous material from a sample for analysis are also well known in this field.

Antibodies for sIP-10 and IP-10

Measuring the levels of sIP-10 expression in a sample is easily undertaken by one knowledgeable in this field. Non-limiting examples include western-blot analysis, ELISA assays, immuno-reactivity assays, column assays using fluorescence, antibodies and radiolabeled markers. Automated manners of performing the analysis, for example, using a computer processor can also be used.

Total, long and short (truncated) IP-10 can be determined utilizing polyclonal (rabbit) and monoclonal (mouse) antibodies that are specific for the long form of IP-10. In an added embodiment, in vivo IP-10 activity can be assessed by using CXCR3 cells as a surrogate for IP-10 activity. Flow cytometry can be used to measure the relative amount of CXCR3 cells in the peripheral blood of patients throughout their treatment. This will serve as a reflection of the ability of activated T cells and B cells to respond to a gradient of IP-10 (keeping in mind that there exist other CXCR3 agonists). In another added embodiment, a dipeptidyl peptidase IV activity can be measured in patient plasma, which can correlate to the IP-10 cleavage.

In this analysis, it is advantageous to inactivate the plasma DPPIV activity, thus preventing an extra-corporeal cleavage of IP-10. Collections are thus preferably performed with protease inhibitors. For example, one such commercially available sample collection tube is BD™ P700 but other such BD™ 100 are also sufficient to preserve IP-10 in its circulating form.

In one embodiment, antibodies specific for the long form of IP-10 to evaluate the amount of long vs. short form of IP-10 are generated. Such antibodies that distinguish full-length IP-10 from short (truncated) form of IP-10, were generated by immunization of rabbits with a synthetic peptide coupled to KLH; (VPLSRTVRC (positions 22-30 of NP_001556; SEQ ID NO: 4) corresponding of the $NH_2$ terminal of the full-length IP-10 protein). Immunoglobulins G (IgG) can then be purified in two steps by chromatography affinity: the first step is a positive selection of IgG that recognize the long peptide. The second step is depletion of IgG that recognize the shorter peptide LSRTVRC (SEQ ID NO: 4) common to short and full-length form of IP-10. Purified antibodies are specific to full-length IP-10. The same strategy can be used to obtain polyclonal antibodies from different species (e.g., goat, chicken, and others). Monoclonal antibodies may also be derived from mice after immunization with the long peptide. After verifying the presence of antibody production in the serum, hybridomas are produced and cloned. The hybridoma screening can be made by direct ELISA with both, the long and short peptides, and the full-length and short form of recombinant IP-10 coated directly in ELISA plate. Then antibodies from hybridomas specific of the full-length can be purified. Validation of polyclonal antibodies can be performed by direct and by sandwiches Elisa assays against short and full-length IP-10 form. SIP-10 can be generated by following in vitro digestion of recombinant full-length IP-10 by recombinant DPIV. The two $NH_2$ amino-acids, Valine and Proline are truncated from the full-length. Monoclonal antibodies discriminating between the short and the long forms of IP-10 have been described in e.g. U.S. Pat. No. 8,124,332 and in Casrouge et al., *J Clin Invest.*, 121(1): 308-317, 2011.

sIP-10 Levels Assay

Using these distinguishing antibodies, IP-10 can be detected in biological fluids, for example, using an ELISA assay to specifically detect the full-length IP-10. As IP-10 binds to heparin, heparin cross-linked to agarose beads via amide bonds can be used to concentrate IP-10 from plasma. IP-10 can be eluted with NaCl 1M. To avoid or at least minimize ex vivo truncation of IP-10 in biologic samples, inhibitors of DPIV can be added into collection tubes. Various DPIV inhibitors are known in the art, e.g., a large number of DPIV inhibitors have been described and their structures and characteristics have been succinctly reviewed (see e.g. U.S. Pat. No. 4,935,493; U.S. Pat. No. 5,462,928; U.S. Pat. No. 5,543,396; U.S. Pat. No. 5,296,604; U.S. Pat. No. 6,100,234; PCT/US92/09845; Augustyns et al., *Curr Med Chem.*, 6(4): 311-327, 1999; Evans, *IDrugs*, 5: 577-585, 2002; Weber, *J Med Chem.*, 47(17): 4135-4141, 2004; McIntosh et al., *Int J Biochem & Cell Biol*, 38(5-6): 860-872, 2006; Wiedeman & Trevillyan, *Curr Opin Investig Drugs*, 4(4): 412-420; 2003). The HuCAl (Human Combinatorial Antibody library) technology allows to generate in vitro a 1.5 billion human antibodies candidates library. An automated panning process is used: the peptides specific of long and short forms of IP-10 are immobilized in 384-well microplate for screening against antibody-displaying phage library. Specificity of antibodies is then verified by ELISA.

To generate the short (truncated) IP-10 form, the full length IP-10 sequence (VPLSRTVRCTCISISNQPVN-PRSLEKLEIIPASQF CPRVEIIATMKKKGEKRCLN-PESKAIKNLLKAVSKEMSKRSP, SEQ ID NO: 1) can be incubated with DPIV at 25-37° C. to generate the short form (LSRTVRCTCISISNQPVNPRSLEKLEIIPASQFCPR VEIIATMKKKGEKRCLNPESKAIKNLLKAVSKEM-SKRSP, SEQ ID NO: 2). DPIV is a known protein, with a cloned sequence (e.g., from mammals such as human and mouse). Resolution of IP-10 and sIP-10 can be accomplished by Western blotting or by MALDI-TOF-MS as is known in the art.

In other embodiments, the antibodies that distinguish between the short and long forms of IP-10 can be used to evaluate patients with chronic inflammation (e.g., cancer, obesity, autoimmunity, graft vs. host disease). Specific applications can be focused on diseases in which IP-10 and/or DPIV have been shown to be elevated (e.g., melanoma, type II diabetes, autoimmune vasculitis).

Soluble DPPIV Expression

Human soluble dipeptidyl peptidase IV (soluble DPPIV) amino acid sequence is shown in SEQ ID NO: 3, and comprises the amino acid positions 29 to 766 from Swissprot database Accession number P27487. The dimer of soluble DPPIV is a 170 kDa glycoprotein consisting of two identical monomeric soluble DPPIV units.

To express a soluble DPPIV enzyme, the polynucleotide can be inserted into an expression vector which contains the necessary elements for the transcription and translation of the inserted coding sequence. Methods which are well known to those skilled in the art can be used to construct expression vectors containing sequences encoding a soluble DPPIV polypeptide and appropriate transcriptional and translational control elements. These methods include in vitro recombinant DNA techniques, synthetic techniques, and in vivo genetic recombination. Such techniques are described, for example, in Sambrook et al. (1989) and in Ausubel et al (1989).

A variety of expression vector/host systems can be utilized to contain and express sequences encoding a soluble DPPIV polypeptide. These include, but are not limited to, microorganisms, such as bacteria transformed with recombinant bacteriophage, plasmid, or cosmid DNA expression vectors; yeast transformed with yeast expression vectors, insect cell systems infected with virus "expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUE-SCRIPT phagemid (Stratagene, LaJolla, Calif.) or pSPORTI plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a soluble DPPIV enzyme polypeptide, vectors based on SV40 or EBV can be used with an appropriate selectable marker.

DPPIV Assay

Assays for DPPIV activity are well known in the art. DPPIV activity can be assayed using a substrate which reacts with DPPIV to form a detectable product, as described in U.S. Pat. No. 5,601,986. Suitable enzyme substrates include, but are not limited to, dipeptide substrates such as Xaa-pro-para-nitro-analide (Xaa-Pro-PNA) or Xaa-Pro-coumarin. The variable amino acid, Xaa, can be any naturally occurring or synthetic amino acid. An exemplary dipeptide substrate is Gly-Pro-para-nitro-analide (Gly-Pro-PNA). At a wavelength of 405 nanometers, the substrate has no absorbance; however, if the dipeptide substrate is cleaved (after the Pro) due to the presence of DPPIV, the formation of a reaction product can be visualized spectrophotometrically, as a yellow-green color is produced. Other substrates, such as Xaa-Pro-coumarin, can be visualized spectrofluorometrically as a fluorescent emission is produced by the reaction.

DPPIV assays embodying such reagents and reactions can be performed in any suitable reaction vessel, for example, a test tube or well of a microtiter plate. Enzyme activities typically are measured at 24° C., by mixing 50 or 100 µl of enzyme sample to 100 or 150 µl microliters of a reaction buffer containing 200 µM of chromogenic substrate, such as Gly-Pro-PNA (commercially available from Bachem, San Diego, Calif.) in 0.1 M Tris-HCl buffered Triton X-100 (0.1% v/v) at pH 7.0. The reactions are incubated for 30 minutes, and optical density readings are taken at 405 nm. During the reaction time course, several optical density readings are taken at different time points. DPPIV enzyme activity is expressed in nmol/min/ml based on the progression curve calculated from the concentration of hydrolyzed substrates.

Methods of Treatment

A subject identified as being infected with HIV and who has a bad prognosis would benefit from being treated with an anti-HIV therapy before the appearance of the AIDS symptoms.

A practitioner treats HIV infection by taking actions to ameliorate the causes or symptoms of the infection in a patient. Treatment of HIV comprises administering therapy to a patient. Therapy may include: selecting and administering one or more anti-HIV drugs to the patient, adjusting the dosage of the anti-HIV drug, adjusting the dosing schedule of the drug, and adjusting the length of the therapy. Anti-HIV drugs are selected by practitioners based on the nature of the infection, the patient's response to the infection and the patient's response to the drug. The dosage of the anti-HIV drug can be adjusted as well by the practitioner based on the nature of the drug, the nature of the infection, the patient's response to the infection, and the patient's response to the drug. The dosing schedule can also be adjusted by the practitioner based on the nature of the drug, the nature of the infection, the patient's response to the infection, and the patient's response to the drug. Also, the length of the therapy can be adjusted by the practitioner based on the nature of the drug, the nature of the infection, the patient's response to the infection, the patient's response to the drug. Also, the practitioner can select between a single drug therapy, a dual drug therapy, or a triple drug therapy. Also, the anti-HIV therapy can be adjusted by the practitioner based on whether the patient suffers from acute HIV infection, chronic HIV infection or AIDS.

Antiretroviral or anti-HIV disease therapy can include, but is not limited to, highly active antiretroviral therapy (HAART), protease inhibitors, fusion inhibitors, integrase inhibitors, co-receptor specific agents, 3TC, AZT, nevirapine, non-nucleoside analogue reverse transcriptase inhibitors and nucleoside analogue reverse transcriptase inhibitors. HAART can be three or more antiretroviral drugs in combination, including at least one protease inhibitor, or at least a reverse transcriptase inhibitor and a protease inhibitor; or at least two reverse transcriptase inhibitors with at least one protease inhibitor.

Typical reverse transcriptase inhibitors include nucleoside analogs, e.g., AZT (Zidovudine), ddi (didanosine), ddc (zalcitabine), D4T (stavudine), 3TC (lamivudine), Ziagen (abacavir), combivir (mix of AZT and 3TC), and non-nucleoside analogs, e.g., viramune (nevirapine), rescriptor (delavirdine), sustiva (efavirenz). Protease inhibitors include invirase (saquinavir), norvir (ritonavir), crixivan (indinavir), viracept (nelfinavir), agenerase (amprenivir), kaletra (lopinavir and ritonavir) and fortovase (saquinavir in a soft gelatin form). Thus, HAART can also be "triple cocktail" therapy. That is, a three drug regimen is used to combat HIV wherein one of the three drugs is usually a protease inhibitor (and the other two are usually reverse transcriptase inhibitors).

In a particular aspect, the invention relates to a method for selecting an anti-HIV therapy for a subject identified as being infected with HIV. Generally, the method of the invention comprises at least the following steps:
  a) determining the likelihood that said subject will develop AIDS by any one of the above methods; and
  b) selecting the therapy based on the said likelihood.

In one embodiment the invention relates to a method for selecting an anti-HIV therapy for a subject identified as being infected with HIV. Generally, the method of the invention comprises at least the following steps:
  a) determining the prognosis of the said subject by any one of the above methods; and
  b) selecting the therapy based on the said prognosis.

In one embodiment the therapy is selected from the group consisting of: highly active antiretroviral therapy (HAART), protease inhibitors, fusion inhibitors, integrase inhibitors, co-receptor specific agents, 3TC, AZT, nevirapine, non-nucleoside analogue reverse transcriptase inhibitors, nucleoside analogue reverse transcriptase inhibitors and vaccine therapy.

HIV-infected subjects who efficiently control viral replication because they are under anti-HIV therapy, e.g. HAART regimen, still display low levels of chronic inflammation. HIV-infected subjects, who interrupt antiretroviral treatment, generally display a strong viral rebound. During this viral rebound, the subjects are highly transmissible for HIV. Interestingly, between 5 and 15% of HIV-infected subjects who started HIV therapy, e.g., HAART, early, spontaneously control viral replication after treatment interruption. More generally, it would be advantageous to be capable of monitoring the efficacy of anti-HIV therapy for subjects identified as being infected with HIV. In particular, it would thus be useful to be capable of identifying the subjects who have a high likelihood of controlling viral replication and not developing AIDS. These subjects would thus benefit from arresting their treatment. Alternatively, it would be useful to identify the subjects who have a high likelihood of progressing towards AIDS if their treatment was stopped. These patients should be maintained on an HIV therapy.

The present invention thus provides a method for monitoring the efficacy of an anti-HIV therapy for a subject identified as being infected with HIV, said method comprising the steps of:
  a) determining the likelihood that said subject will develop AIDS by any one of the above methods; and
  b) assessing the efficacy of said therapy based on the determination of step a).

Efficacy of HIV treatment can be determined using the methods provided herein. In particular examples, the level of sIP-10 or the ratio of sIP-10 to total IP-10 or the activity of DPPIV is measured at a first time point using the methods provided and then compared to the level of sIP-10 or the ratio of sIP-10 to total IP-10 or the activity of DPPIV, respectively, measured at a second later time point by the same method. In some examples, the first time point is at a predetermined time prior to administration of a therapy, such as an anti-HIV therapy, and the second time point is at a predetermined time following administration of the therapy, during the administration of the therapy, or between successive administrations of the therapy. In exemplary methods, the sample can be obtained from the subject, for example, at least, at about or at 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, or later following administration of the anti-HIV therapy to the subject. In some examples, samples are collected at a plurality of time points, such as at more than one time point, including, for example, at 1, 2, 3, 4, 5, 6, 7, 8, 9, 10, 15, 20 or more time points following administration of the anti-HIV therapy to the subject. In some examples, samples are collected at regular intervals following administration of the anti-HIV therapy to the subject.

In particular examples, the level of sIP-10 or the ratio of sIP-10 to total IP-10 or the activity of DPPIV is measured at a first time and then compared to the level of sIP-10 or the ratio of sIP-10 to total IP-10 or the activity of DPPIV, respectively, measured at a second later time point to determine the likelihood of developing AIDS over time, where if the level of sIP-10 or the ratio of sIP-10 to total IP-10 or the activity of DPPIV at the second time point is more than the level of sIP-10 or the ratio of sIP-10 to total IP-10 or the activity of DPPIV, respectively, at the first time point, then the likelihood that the subject will develop AIDS has decreased. In particular examples, if the level of sIP-10 or the ratio of sIP-10 to total IP-10 or the activity of DPPIV at a second time point is 2, 3, 4, 5, 6, 7, 8, 8, 9, 10, 20, 30, 40, 50, 60, 70, 80, 90, 100, 200, 300, 400, 500, 600, 700, 800, 900, 1000 or more times greater than the level of sIP-10 or the ratio of sIP-10 to total IP-10 or the activity of DPPIV, respectively, at a first time point, then the likelihood that the subject will develop AIDS has decreased.

In particular examples, the level of sIP-10 or the ratio of sIP-10 to total IP-10 or the activity of DPPIV is measured at a first time and then compared to the level of sIP-10 or the ratio of sIP-10 to total IP-10 or the activity of DPPIV, respectively, measured at a second later time point to determine stabilization of the likelihood to progress towards AIDS over time, where if the level of sIP-10 or the ratio of sIP-10 to total IP-10 or the activity of DPPIV at the second time point is equal to or about the same as the level of sIP-10 or the ratio of sIP-10 to total IP-10 or the activity of DPPIV at the first time point, then the likelihood to progress towards AIDS has stabilized.

In particular examples, the level of sIP-10 or the ratio of sIP-10 to total IP-10 or the activity of DPPIV is measured at a first time point and then compared to the level of sIP-10 or the ratio of sIP-10 to total IP-10 or the activity of DPPIV, respectively, measured at a second later time point to determine the effectiveness of therapy in inhibiting HIV disease progression, where if the level of sIP-10 or the ratio of sIP-10 to total IP-10 or the activity of DPPIV at the second time point is more than or equal to the level of sIP-10 or the ratio of sIP-10 to total IP-10 or the activity of DPPIV, respectively, at the first time point, then the therapy is effective at inhibiting HIV disease progression. In particular examples, if the level of sIP-10 or the ratio of sIP-10 to total IP-10 or the activity of DPPIV at a second time point is equal to or 2, 3, 4, 5, 6, 7, 8, 8, 9, 10, 20, 30, 40, 50, 60, 70, 80, 90, 100, 200, 300, 400, 500, 600, 700, 800, 900, 1000 or more times greater than the level of sIP-10 or the ratio of sIP-10 to total IP-10 or the activity of DPPIV, respectively, at a first time point, then the therapy is effective at inhibiting HIV disease progression.

In particular examples, the level of sIP-10 or the ratio of sIP-10 to total IP-10 or the activity of DPPIV is measured at a first time point and then compared to the level of sIP-10 or the ratio of sIP-10 to total IP-10 or the activity of DPPIV, respectively, measured at a second later time point to determine the effectiveness of therapy in inhibiting HIV disease progression, where if the level of sIP-10 or the ratio of sIP-10 to total IP-10 or the activity of DPPIV at the first time point is greater than the level of sIP-10 or the ratio of sIP-10 to total IP-10 or the activity of DPPIV, respectively, at the second time point, then the therapy is not effective at inhibiting HIV disease progression. In particular examples, if the level of sIP-10 or the ratio of sIP-10 to total IP-10 or the activity of DPPIV at a first time point is 2, 3, 4, 5, 6, 7, 8, 8, 9, 10, 20, 30, 40, 50, 60, 70, 80, 90, 100, 200, 300, 400, 500, 600, 700, 800, 900, 1000 or more times greater than the level of sIP-10 or the ratio of sIP-10 to total IP-10 or the activity of DPPIV, respectively, at a second time point, then the therapy is not effective at inhibiting HIV disease progression.

In some examples, the methods provided herein can detect at or about a 2-fold, 3-fold, 4-fold, 5-fold, 6-fold, 7-fold, 8-fold, 9-fold, 10-fold, 200-fold, 300-fold, 400-fold, 500-fold, 600-fold, 700-fold, 800-fold, 900-fold, 1000-fold or higher increase in the level of sIP-10 or the ratio of sIP-10 to total IP-10 or the activity of DPPIV over time relative to a control sample. in particular examples, the methods provided herein can detect at or about a 2-fold, 3-fold, 4-fold, 5-fold, 6-fold, 7-fold, 8-fold, 9-fold, 10-fold, 200-fold, 300-fold, 400-fold, 500-fold, 600-fold, 700-fold, 800-fold, 900-fold, 1000-fold or higher decrease in the level of sIP-10 or the ratio of sIP-10 to total IP-10 or the activity of DPPIV over time relative to a control sample. In some examples, the control sample is a sample obtained from a subject at a first time point and compared to a sample obtained from the subject at a second time point. In some examples, the control sample is a sample with a known level of sIP-10 or ratio of sIP-10 to total IP-10 or activity of DPPIV. In some examples, the control sample is a sample obtained from a subject with a particular HIV disease, a known stage of HIV disease, or a known HIV disease prognosis.

The present invention further relates to a method for adjusting a HIV therapy for a subject identified as being infected with HIV, said method comprising the steps of:
 a) assessing the efficacy of an anti-HIV therapy for said subject by any one of the above methods; and
 b) adapting the said treatment based on said assessment.
Said adaptation of the HIV therapy may consist in:
 a reduction or suppression of the said HIV therapy if the therapy is assessed as being effective, or
 the continuation or an augmentation of the said HIV therapy if the therapy is assessed as not being effective.

In one embodiment, the practitioner adjusts the therapy based on the patient's level of sIP-10 or ratio of sIP-10 to total IP-10 or activity of DPPIV compared to a reference level. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In one embodiment, therapy comprises the selection and administration of an anti-HIV drug to the patient by the practitioner. In one embodiment, the anti-HIV disease drug comprises protease inhibitors. In one embodiment, the anti-HIV disease drug comprises fusion inhibitors. In one embodiment, the anti-HIV disease drug comprises integrase inhibitors. In one embodiment, the anti-HIV disease drug comprises co-receptor specific agents. In one embodiment, the anti-HIV disease drug comprises 3TC. In one embodiment, the anti-HIV disease drug antiviral interferon comprises AZT. In one embodiment, the anti-HIV disease drug comprises polymerase inhibitor. In one embodiment, the anti-HIV disease drug comprises protease inhibitor. In one embodiment, the anti-HCV drug comprises nevirapine. In one embodiment, the anti-HIV disease drug comprises non-nucleoside analogue reverse transcriptase inhibitors. In one embodiment, the anti-HIV disease drug comprises nucleoside analogue reverse transcriptase inhibitors.

In another embodiment, therapy comprises the selection and administration of two anti-HIV disease drugs to the patient by the practitioner as part of dual therapy. In one embodiment the two dual therapy drugs are protease inhibitors. In one embodiment the two dual therapy drugs are non-nucleoside analogue reverse transcriptase inhibitors. In one embodiment the two dual therapy drugs are nucleoside analogue reverse transcriptase inhibitors. In one embodiment the two dual therapy drugs are a protease inhibitor and a non-nucleoside analogue reverse transcriptase inhibitor. In one embodiment the two dual therapy drugs are a protease inhibitor and a nucleoside analogue reverse transcriptase inhibitor. In one embodiment the two dual therapy drugs are a non-nucleoside analogue reverse transcriptase inhibitor and nucleoside analogue reverse transcriptase inhibitor.

In another embodiment, therapy comprises the selection and administration of three anti-HIV disease drugs to the patient by the practitioner as part of triple therapy. In one embodiment the three triple therapy drugs are an interferon drug, ribavirin, and a NS3 protease inhibitor. In one embodiment, the triple therapy drugs comprise highly active antiretroviral therapy (HAART). In one embodiment, the anti-HIV disease drug comprises HAART, said HAART being three or more antiretroviral drugs in combination, including at least one protease inhibitor. In one embodiment, the anti-HIV disease drug comprises HAART, said HAART being three or more antiretroviral drugs in combination, including at least a reverse transcriptase inhibitor and a protease inhibitor. In one embodiment, the anti-HIV disease drug comprises HAART, said HAART being three or more antiretroviral drugs in combination, including at least two reverse transcriptase inhibitors with at least one protease inhibitor.

In one embodiment where there is an decreased level of level of sIP-10 or ratio of sIP-10 to total IP-10 or activity of DPPIV with respect to a reference level, treatment comprises a less aggressive therapy than a reference therapy. In one embodiment a less aggressive therapy comprises not administering drugs and taking a "watchful waiting" approach. In one embodiment a less aggressive therapy comprises delaying administration of anti-HIV disease drugs. In one embodiment a less aggressive therapy comprises selecting and administering less potent drugs. In one embodiment a less aggressive therapy comprises decreasing dosage of anti-HIV disease drugs. In one embodiment a less aggressive therapy comprises decreasing the frequency of the dose schedule. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decreasing dose schedule. In one embodiment, less aggressive therapy comprises selecting and administering less potent drugs and shortening length of therapy. In one embodiment, less aggressive therapy comprises decreasing drug dosage and decreasing dose schedule. In one embodiment, less aggressive therapy comprises decreasing drug dosage and shortening length of therapy. In one embodiment, less aggressive therapy comprises decreasing dose schedule and shortening length of therapy. In one embodiment, less aggressive therapy comprises selecting and administering less potent drugs, decreasing drug dosage, and decreasing dose schedule. In one embodiment, less aggressive therapy comprises selecting and administering less potent drugs, decreasing drug dosage, and shortening length of therapy. In one embodiment, less aggressive therapy comprises selecting and administering less potent drugs, decreasing dose schedule, and shortening length of therapy. In one embodiment, less aggressive therapy comprises decreasing drug dosage, decreasing dose schedule, and shortening length of therapy. In one embodiment, less aggressive therapy comprises selecting and administering less potent drugs, decreasing drug dosage, decreasing dose schedule, and shortening length of therapy.

In one embodiment a less aggressive therapy comprises selecting and administering a single therapy instead of a dual therapy. In one embodiment a less aggressive therapy comprises delaying administration of anti-HIV disease drugs and selecting and administering a single therapy instead of a dual therapy. In one embodiment a less aggressive therapy comprises selecting and administering a single therapy instead of a dual therapy and selecting and administering less potent drugs. In one embodiment a less aggressive therapy comprises selecting and administering a single therapy instead of a dual therapy and decreasing dosage of anti-HIV disease drugs. In one embodiment a less aggressive therapy comprises selecting and administering a single therapy instead of a dual therapy and decreasing the frequency of the dose schedule. In one embodiment a less aggressive therapy comprises selecting and administering a single therapy instead of a dual therapy and shortening length of therapy. In one embodiment, less aggressive therapy comprises selecting and administering a single therapy instead of a dual therapy and selecting and administering less potent drugs and decreasing drug dosage. In one embodiment, less aggressive therapy comprises selecting and administering a single therapy instead of a dual therapy and selecting and administering less potent drugs and decreasing dose schedule. In one embodiment, less aggressive therapy comprises selecting and administering a single therapy instead of a dual therapy, selecting and administering less potent drugs and shortening length of therapy. In one embodiment, less aggressive therapy comprises selecting and administering a single therapy instead of a dual therapy, decreasing drug dosage and decreasing dose schedule. In one embodiment, less aggressive therapy comprises selecting and administering a single therapy instead of a dual therapy, decreasing drug dosage and shortening length of therapy. In one embodiment, less aggressive therapy comprises selecting and administering a single therapy instead of a dual therapy, decreasing dose schedule and shortening length of therapy. In one embodiment, less aggressive therapy comprises selecting and administering a single therapy instead of a dual therapy, selecting and administering less potent drugs, decreasing drug dosage, and decreasing dose schedule. In one embodiment, less aggressive therapy comprises selecting and administering a single therapy instead of a dual therapy, selecting and administering less potent drugs, decreasing drug dosage, and shortening length of therapy. In one embodiment, less aggressive therapy comprises selecting and administering a single therapy instead of a dual therapy, selecting and administering less potent drugs, decreasing dose schedule, and shortening length of therapy. In one embodiment, less aggressive therapy comprises selecting and administering a single therapy instead of a dual therapy, decreasing drug dosage, decreasing dose schedule, and shortening length of therapy. In one embodiment, less aggressive therapy comprises selecting and administering a single therapy instead of a dual therapy, selecting and administering less potent drugs, decreasing drug dosage, decreasing dose schedule, and shortening length of therapy. In one embodiment a less aggressive therapy comprises selecting and administering a single therapy instead of a dual therapy.

In one embodiment a less aggressive therapy comprises selecting and administering a dual therapy instead of a triple therapy. In one embodiment a less aggressive therapy comprises selecting and administering a dual therapy instead of a triple therapy and delaying administration of anti-HIV disease drugs. In one embodiment a less aggressive therapy comprises selecting and administering a dual therapy instead of a triple therapy and selecting and administering less potent drugs. In one embodiment a less aggressive therapy comprises selecting and administering a dual therapy instead of a triple therapy and decreasing dosage of anti-HIV disease drugs. In one embodiment a less aggressive therapy comprises selecting and administering a dual therapy instead of a triple therapy and decreasing the frequency of the dose schedule. In one embodiment a less aggressive therapy comprises selecting and administering a dual therapy instead of a triple therapy and shortening length of therapy. In one embodiment, less aggressive therapy comprises selecting and administering a dual therapy instead of a triple therapy, selecting and administering less potent drugs and decreasing drug dosage. In one embodiment, less aggressive therapy comprises selecting and administering a dual therapy instead of a triple therapy, selecting and administering less potent drugs and decreasing dose schedule. In one embodiment, less aggressive therapy comprises selecting and administering a dual therapy instead of a triple therapy, selecting and administering less potent drugs and shortening length of therapy. In one embodiment, less aggressive therapy comprises selecting and administering a dual therapy instead of a triple therapy, decreasing drug dosage and decreasing dose schedule. In one embodiment, less aggressive therapy comprises selecting and administering a dual therapy instead of a triple therapy, decreasing drug dosage and shortening length of therapy. In one embodiment, less aggressive therapy comprises selecting and administering a dual therapy instead of a triple therapy, decreasing dose schedule and shortening length of therapy. In one embodiment, less aggressive therapy comprises selecting and administering a dual therapy instead of a triple therapy, selecting and administering less potent drugs, decreasing drug dosage, and decreasing dose schedule. In one embodiment, less aggressive therapy comprises selecting and administering a dual therapy instead of a triple therapy, selecting and administering less potent drugs, decreasing drug dosage, and shortening length of therapy. In one embodiment, less aggressive therapy comprises selecting and administering a dual therapy instead of a triple therapy, selecting and administering less potent drugs, decreasing dose schedule, and shortening length of therapy. In one embodiment, less aggressive therapy comprises selecting and administering a dual therapy instead of a triple therapy, decreasing drug dosage, decreasing dose schedule, and shortening length of therapy. In one embodiment, less aggressive therapy comprises selecting and administering a dual therapy instead of a triple therapy, selecting and administering less potent drugs, decreasing drug dosage, decreasing dose schedule, and shortening length of therapy.

In one aspect of the present application where there is an increased level of level of sIP-10 or ratio of sIP-10 to total IP-10 or activity of DPPIV with respect to a reference level, treatment comprises a more aggressive therapy than a reference therapy. In one embodiment a more aggressive therapy comprises earlier administration of anti-HIV disease drugs. In one embodiment a more aggressive therapy comprises increased dosage of anti-HIV disease drugs. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and increasing dose schedule. In one embodiment, more aggressive therapy comprises selecting and administering more potent drugs and increasing length of therapy. In one embodiment, more aggressive therapy comprises increasing drug dosage and increasing dose schedule. In one embodiment, more aggressive therapy comprises increasing drug dosage and increasing length of therapy. In one embodiment, more aggressive therapy comprises increasing dose schedule and increasing length of therapy. In one embodiment, more aggressive therapy comprises selecting and administering more potent drugs, increasing drug dosage, and increasing dose schedule. In one embodiment, more aggressive therapy comprises selecting and administering more potent drugs, increasing drug dosage, and increasing length of therapy. In one embodiment, more aggressive therapy comprises selecting and administering more potent drugs, increasing dose schedule, and increasing length of therapy. In one embodiment, more aggressive therapy comprises increasing drug dosage, increasing dose schedule, and increasing length of therapy. In one embodiment, more aggressive therapy comprises selecting and administering more potent drugs, increasing drug dosage, increasing dose schedule, and increasing length of therapy.

In one embodiment a less aggressive therapy comprises selecting and administering a dual therapy instead of a single therapy. In one embodiment a more aggressive therapy comprises selecting and administering a dual therapy instead of a single therapy and earlier administration of anti-HIV disease drugs. In one embodiment a more aggressive therapy comprises selecting and administering a dual therapy instead of a single therapy and increased dosage of anti-HIV disease drugs. In one embodiment a more aggressive therapy comprises selecting and administering a dual therapy instead of a single therapy and increased length of therapy. In one embodiment a more aggressive therapy comprises selecting and administering a dual therapy instead of a single therapy and increased frequency of the dose schedule. In one embodiment, more aggressive therapy comprises selecting and administering a dual therapy instead of a single therapy, selecting and administering more potent drugs and increasing drug dosage. In one embodiment, more aggressive therapy comprises selecting and administering a dual therapy instead of a single therapy, selecting and administering more potent drugs and increasing dose schedule. In one embodiment, more aggressive therapy comprises selecting and administering a dual therapy instead of a single therapy, selecting and administering more potent drugs and increasing length of therapy. In one embodiment, more aggressive therapy comprises selecting and administering a dual therapy instead of a single therapy, increasing drug dosage and increasing dose schedule. In one embodiment, more aggressive therapy comprises selecting and administering a dual therapy instead of a single therapy, increasing drug dosage and increasing length of therapy. In one embodiment, more aggressive therapy comprises selecting and administering a dual therapy instead of a single therapy, increasing dose schedule and increasing length of therapy. In one embodiment, more aggressive therapy comprises selecting and administering a dual therapy instead of a single therapy, selecting and administering more potent drugs, increasing drug dosage, and increasing dose schedule. In one embodiment, more aggressive therapy comprises selecting and administering a dual therapy instead of a single therapy, selecting and administering more potent drugs, increasing drug dosage, and increasing length of therapy. In one embodiment, more aggressive therapy comprises selecting and administering a dual therapy instead of a single therapy, selecting and administering more potent drugs, increasing dose schedule, and increasing length of therapy. In one embodiment, more aggressive therapy comprises selecting and administering a dual therapy instead of a single therapy, increasing drug dosage, increasing dose schedule, and increasing length of therapy. In one embodiment, more aggressive therapy comprises selecting and administering a dual therapy instead of a single therapy, selecting and administering more potent drugs, increasing drug dosage, increasing dose schedule, and increasing length of therapy.

In one embodiment a more aggressive therapy comprises selecting and administering a triple therapy instead of a dual therapy. In one embodiment a more aggressive therapy comprises selecting and administering a triple therapy instead of a dual therapy and earlier administration of anti-HIV disease drugs. In one embodiment a more aggressive therapy comprises selecting and administering a triple therapy instead of a dual therapy and increased dosage of anti-HIV disease drugs. In one embodiment a more aggressive therapy comprises selecting and administering a triple therapy instead of a dual therapy and increased length of therapy. In one embodiment a more aggressive therapy comprises selecting and administering a triple therapy instead of a dual therapy and increased frequency of the dose schedule. In one embodiment, more aggressive therapy comprises selecting and administering a triple therapy instead of a dual therapy, selecting and administering more potent drugs and increasing drug dosage. In one embodiment, more aggressive therapy comprises selecting and administering a triple therapy instead of a dual therapy, selecting and administering more potent drugs and increasing dose schedule. In one embodiment, more aggressive therapy comprises selecting and administering a triple therapy instead of a dual therapy, selecting and administering more potent drugs and increasing length of therapy. In one embodiment, more aggressive therapy comprises selecting and administering a triple therapy instead of a dual therapy, increasing drug dosage and increasing dose schedule. In one embodiment, more aggressive therapy comprises selecting and administering a triple therapy instead of a dual therapy, increasing drug dosage and increasing length of therapy. In one embodiment, more aggressive therapy comprises selecting and administering a triple therapy instead of a dual therapy, increasing dose schedule and increasing length of therapy. In one embodiment, more aggressive therapy comprises selecting and administering a triple therapy instead of a dual therapy, selecting and administering more potent drugs, increasing drug dosage, and increasing dose schedule. In one embodiment, more aggressive therapy comprises selecting and administering a triple therapy instead of a dual therapy, selecting and administering more potent drugs, increasing drug dosage, and increasing length of therapy. In one embodiment, more aggressive therapy comprises selecting and administering a triple therapy instead of a dual therapy, selecting and administering more potent drugs, increasing dose schedule, and increasing length of therapy. In one embodiment, more aggressive therapy comprises selecting and administering a triple therapy instead of a dual therapy, increasing drug dosage, increasing dose schedule, and increasing length of therapy. In one embodiment, more aggressive therapy comprises selecting and administering a triple therapy instead of a dual therapy, selecting and administering more potent drugs, increasing drug dosage, increasing dose schedule, and increasing length of therapy.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting. Other features and advantages of the invention will be apparent from the following detailed description, and from the claims.

EXAMPLES

Total IP-10 Expression is Rapidly Controlled During Non-Pathogenic SIV Infection We searched for factors involved in the lack of chronic immune activation in the AGM animal model. We showed that AGM, during acute SIV infection, display signs of inflammation. For instance, AGM produce IFN-α and IFN-γ upon SIVagm infection. However this inflammation is only observed during the first weeks post-infection and does not persist (Kornfeld et al., *J Clin Invest.*, 115(4): 1082-1091, 2005; Ploquin et al., *Retrovirology*, 3: 37, 2006; Diop et al., *J Virol.*, 82(11): 5145-5152, 2008). Our data therefore revealed that AGM do not lack but rather regulate inflammation.

The capacity of natural hosts to mount an inflammation during acute infection was highly disputed in the literature. In order to further demonstrate that AGM do not lack the capacity to sensor SIVagm infection and mount an innate immune response, we performed a trancriptome analysis. Among other genes, we measured the expression profiles of Interferon-stimulated genes (ISG), which are considered as surrogate markers for IFN activity. We and others demonstrated a rapid and strong induction of ISGs, including IP-10 (Jacquelin et al., *J Clin Invest*, 119(12): 3544-3555, 2009; Favre et al., *PLoS Pathog.*, 5(2): e1000295, 2009). Interestingly, in contrast to pathogenic SIVmac infection in macaques, the expression of IP-10 was transient in AGM, in contrast to macaques, where IP-10 expression remains highly elevated (Jacquelin et al., *J Clin Invest*, 119(12): 3544-3555, 2009; Favre et al., *PLoS Pathog.*, 5(2): e1000295, 2009) (FIG. 1).

Plasma Total IP-10 Levels During Acute HIV-1 Infection are Stronger Predictors of Disease Progression than Viremia and $CD4^+$ T Cell Counts The data on the differences between pathogenic and non-pathogenic SIV infection has lead us raise the hypothesis that uncontrolled inflammation and IFN response at the end of acute HIV infection could be of bad prognosis for disease progression in HIV-infected individuals. The concentrations of 28 plasma proteins, including IFN-I inducible proteins and anti-inflammatory cytokines, were quantified during acute HIV-1 infection of 133 non-treated patients. This was a retrospective study, and the disease progression profiles of each patient were known (Liovat et al., Keystone Symposium on HIV Evolution, Genomics and Pathogenesis. Whistler, Canada; 2011; Liovat et al., 6th IAS Conference on HIV pathogenesis, treatment and prevention. Rome; 2011; Liovat et al., PLoS One, 7(10): e46143, 2012). This study revealed for the first time an association between inflammation in acute infection and T cell activation at set-point (i.e. 6 months post-infection). Moreover, IP-10 was an independent predictor of rapid disease progression. Of note, when measured in acute HIV-1 infection, IP-10 robustness of prediction was stronger than that of viremia or $CD4^+$ T cell counts.

Only two other studies had analysed before the predictive capacity of inflammatory molecules during acute HIV infection to predict subsequent disease progression. Roberts et al did not identify an association of IP-10 with disease progression (Roberts et al., Aids, 24(6): 819-31, 2010), while Jiao showed a predictive value of early IP-10 levels for $CD4^+$ T cell loss in a cohort of Chinese patients (Jiao et al., Viral Immunol., 25(4): 333-337, 2012). Other studies had evaluated IP-10 in chronic phase of infection or after treatment and had a found a negative correlation with $CD4^+$ T cell counts and a strong association with viremia levels (Kamat et al., PLoS One, 7(2): e30881, 2012; Keating et al., Aids, 25(15): 1823-32, 2011). Our data indicate for the first time that when measured in acute HIV-1 infection, IP-10 robustness of prediction is stronger than that of VL and $CD4^+$ T cell counts (Liovat et al., PLoS One, 7(10): e46143, 2012) (FIG. 2).

The Plasma IP-10 Level During Acute HIV-1 Infection is a Stronger Predictor of Disease Progression than the Viral Reservoir Size In order to further demonstrate the robustness of prediction of IP-10, we wanted to compare it to other markers that have been associated with disease progression. We already compared it above to viral RNA levels in plasma. In recent times, numerous studies stressed the importance of the viral DNA levels, which are associated with the number of infected cells. Indeed, the viral DNA copy numbers correspond to the so-called viral reservoir. The size of this viral reservoir reflects the host's capacity to control viral replication, infection and spread. The size of the viral reservoir is remarkably low in HIV controllers and in post-treatment controllers. It has been suggested that an early/immediate start of HAART after HIV infection is of benefit for the patients because it might limit the viral reservoir. A study carried out on 22 patients enrolled during acute HIV infection, showed that after several months of HAART, among 22 analytes measured, only IP-10 differed significantly between treated and non-treated participants (Gay et al., PLoS One, 6(5): e19617, 2011).

We are currently collaborating with Pr. Christine Rouzioux (Hôpital Necker). Her team had quantified the viral DNA load in the same patients, where we had quantified total IP-10 levels. The levels of IP-10 and viral DNA in acute infection were correlated (R=0.35 p=0.0001). In multivariate analyses, the plasma levels of IP-10 during acute infection remained highly predictive of rapid progression towards AIDS (p=0.003), while viral DNA levels were not (p=0.47). This supports our previous findings on IP-10 being a robust and early predictor of disease progression (FIG. 2).

The Plasma IP-10 Level Before HIV-1 Infection Predicts the Rate of CD4+ T Cell Loss after Infection In order to validate our results in an independent cohort, we contacted the coordinator of the Amsterdam Cohort studies (ACS) in Netherlands. The ACS are recognized as one of the oldest and biggest HIV-1 cohorts. A rare feature is that for hundreds of HIV patients, blood samples collected before infection are available in the ACS. We thus quantified IP-10 in plasma at different time points before and after HIV-1 infection in 136 non-treated patients. The IP-10 levels before infection correlated with the levels 6 months after HIV infection (R=0.37 p=0.003). Of note, the levels of IP-10 within the 25 months before infection were predictive of rapid disease progression upon HIV-1 infection (OR=3.18 95%1.06-9.55 p=0.03).

The Ratio of the Antagonist Form of IP-10 (Short IP-10) is Decreased in Acute HIV-1 Infection in Patients Who Subsequently Progress Rapidly Towards AIDS By measuring total IP-10, as we did above, one cannot distinguish between distinct IP-10 forms, i.e. short and long forms. During HCV infection, high levels of plasma IP-10 are predictive of the failure to respond to peg-IFN-$a_2$/RBV therapy (Casrouge et al., J Clin Invest., 121(1): 308-317, 2011). Investigators in the Albert laboratory demonstrated that these elevated IP-10 levels are mainly in the short antagonist form. This increased IP-10 antagonism prevents trafficking of CXCR3+ lymphocytes capable to control HCV replication, to the liver, thus diminishing HCV control and explains the failure of response to peg-IFN-$a_2$/RBV treatment ((Casrouge et al., J Clin Invest., 121(1): 308-317, 2011; Casrouge et al., Clin Exp Immunol., 167(1): 137-148, 2012). We hypothesized that progressive HIV/SIV infections are associated with decreased IP-10 antagonism, thus enhancing CXCR3+ lymphocyte trafficking into lymphoid organs and the gut mucosa amplifying inflammation during HIV/SIV infection. This model would be the opposite picture of what has been suggested for HCV infection, where high levels of IP-10 antagonist form are harmful, while in HIV infection they would limit inflammation and play a protective role.

To address this question we started to evaluate the concentrations of IP-10 antagonist form in plasma from acutely HIV-infected individuals (ANRS Primo C06 cohort). Using a standardized ELISA developed in Matthew Albert's laboratory consisting of a specific antibody raised against the IP-10 antagonist form (Casrouge et al., J Clin Invest., 121(1): 308-317, 2011), we performed a preliminary evaluation of 53 samples. The ratio of short versus total IP-10 antagonist was decreased during acute HIV-1 infection in rapid progressors compared to the other HIV-infected patients, and also compared to healthy donors (p<0.01) (FIG. 3).

There was a trend for a positive correlation (R=0.31 p=0.0575) between short IP-10 in acute infection and the CD4 T-cell counts at set-point 6 months later (M6). Moreover, the ratios of short against total IP-10 in acute infection negatively correlated (R=0.4764 p=0.0494) with CD8 T-cell activation at M6.

Figure 4:
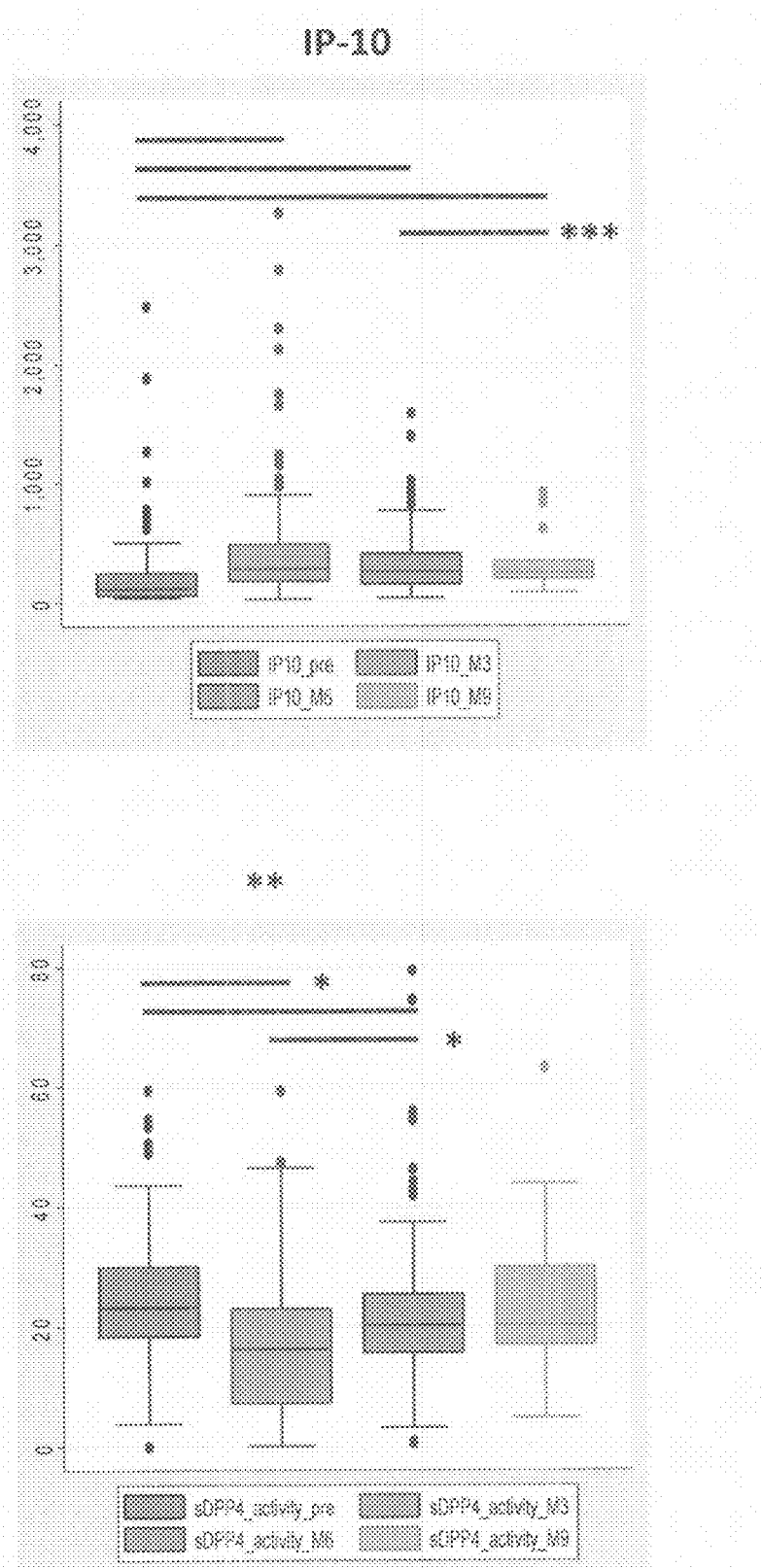
FIG. 4: Dynamics of plasma total IP-10 and sDPPIV-like activity after seroconversion in HIV-1 infected individuals. Frozen sera collected on EDTA were obtained from 134 HIV$^+$ patients at 3 (M3), 6 (M6) or 9 (M9) months post alleged date of seroconversion or even before infection (Pre). Patients were enrolled in the Amsterdam cohort Studies on HIV/AIDS. Total IP10 concentrations were measured as previously described (Liovat et al., *PLoS One,* 7(10): e46143, 2012). We also monitored the bioactive sDPPIV titers in plasma, determined with a luminescence-based assay (Promega). Wilcoxon signed rank test was used to compare time points.

The Activity of DPPIV is Reduced During Acute Infection of Rapid Disease Progressors Next, we wondered which factors could be responsible for the distinct levels of IP-10 among the individuals. The Dipeptidyl peptidase IV (DPPIV) is known to cleave IP-10 into the short IP-10 form. It has already been shown that DPPIV is decreased in the blood of patients chronically infected by HIV (Blazquez et al., J Immunol., 149(9):

3073-3077, 1992; De Pasquale et al., *Acta Haematol.*, 81(1): 19-21, 1989; Gougeon et al., *Res Immunol.*, 147(1): 5-8, 1996; Vanham et al., *J Acquir Immune Defic Syndr,* 6(7): 749-757, 1993). We quantified DPPIV for the first time in acute HIV-1 infection. Importantly, we evaluated DPPIV in patients showing three distinct types of disease progression profile: slow progression, normal progression and rapid progression towards AIDS. Soluble DPPIV activity was measured in 53 patients of the ANRS Primo Cohort No 6 and 134 patients of the ACS. The plasma levels of soluble DPPIV were significantly reduced during acute HIV infection in both cohorts (FIGS. 3 and 4). The levels were significantly lower in rapid disease progressors than in normal or slow progressors. Indeed the levels measured in acute HIV-1 infection were predictive of rapid disease progression (OR=3.27 95%1.05-10.16 p=0.04). Further, the plasmas levels of soluble DPPIV (measured in sera samples from the ACS cohort) at 6 months after seroconversion had predictive value for rapid disease progression (OR=1.88 95%1.03-3.45 p=0.04), The robustness was weaker as observed in the ANRS cohort might be due to measurements carried out at a later time point. Thus, our study reveals distinct levels of DPPIV according to the disease progression profile.

In line with this, the plasma levels of soluble DPPIV (measured in plasma samples from the ANRS cohort) at primary HIV infection correlated negatively with viremia as well as with T cell activation at set-point ((p=0.003, R=−0.76 and p=0.049, R=−0.42, respectively).

Ultimately, these data suggest that decreased levels of IP-10 antagonist form and sDPPIV activity badly influence the viral and immunologic set-points. In other words, preserving sDPPIV activity leading to high levels of IP-10 antagonist would be of good prognosis for HIV-1 infection.

Higher Inflammation in the Gut of SIV-Infected Macaques is Associated with Lower Expression of DPPIV In order to confirm the link between DPPIV and AIDS pathogenesis, we initiated a study to address this in simian models. We sampled gut tissue from SIV-infected MAC (n=6) and AGM (n=5) at day 65 p.i. This corresponds to an interesting time point as it is situated shortly after acute infection, when IP-10 levels are already differently regulated between MAC and AGM (Jacquelin et al., *J Clin Invest,* 119(12): 3544-3555, 2009). We harvested fragments of jejunum, ileum, colon and rectum. We quantified IP-10 gene expression levels in enriched intra-epithelial (IEC) and CD4$^+$ cells of each of these compartments. IP-10 was significantly more expressed in the high intestine than in colon/rectum. We also detected an over-representation of CXCR3 gene transcripts in CD4+ cells from the MAC high intestine.

Figure 5:
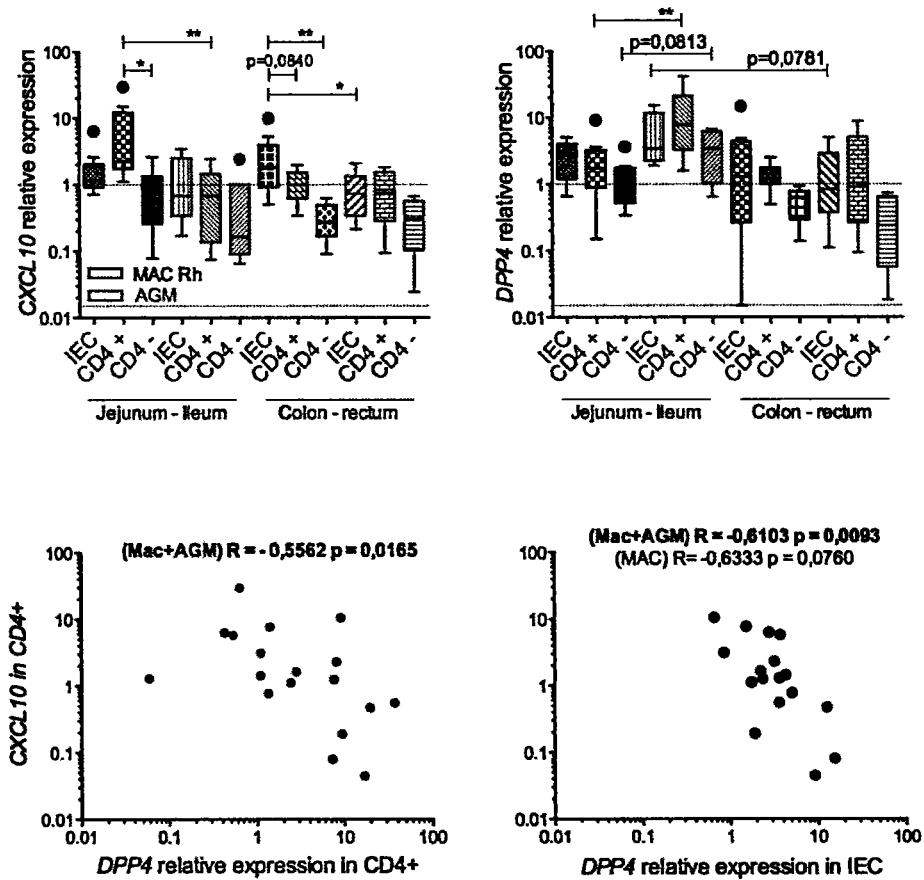
FIG. 5: IP-10 and DPPIV gene expression levels in the gut of SIV-infected MAC and AGM. We sampled gut tissue at the time point of euthanasia in SIVmac-infected MAC (n=6) and SIVagm-infected AGM (n=5) used in other research projects. These necropsies were performed at day 65 p.i., when inflammatory profiles are already distinct between MAC and AGM. We harvested fragments of jejunum, ileum, colon and rectum. Gut intra-epithelial cells (IEC) and gut mucosal CD4$^+$ and CD4$^{neg}$ cells were enriched after collagenase digestion, centrifugation on a Percoll gradient followed by a CD4 enrichment using magnetic beads. Gene transcript expression was determined by RT-PCR using Taqman gene expression assays. Relative expressions were normalized first against 18sRNA. On the top panel, Mann-Whitney test and Wilcoxon signed-rank test were used to compare compartments between species or within each species, respectively. On bottom panel, correlations were determined using the Spearman test on normalized values obtained in the specified cell compartment enriched from the high intestine (jejunum/Ileum) of each animal against values obtained in the specified cell compartment enriched from the rectum of each animal.

Equally in accordance with our hypothesis, DPP4 gene expression was less pronounced in CD4$^+$ cells from MAC than in AGM (FIG. 5). There was a significant negative correlation between DPPIV in CD4$^+$ and in IEC with IP-10 gene expression in the CD4$^+$ compartment of the high intestine (FIG. 5).

Altogether, lower IP-10 inflammation in the gut was associated with higher levels of DPPIV.

Figure 6:
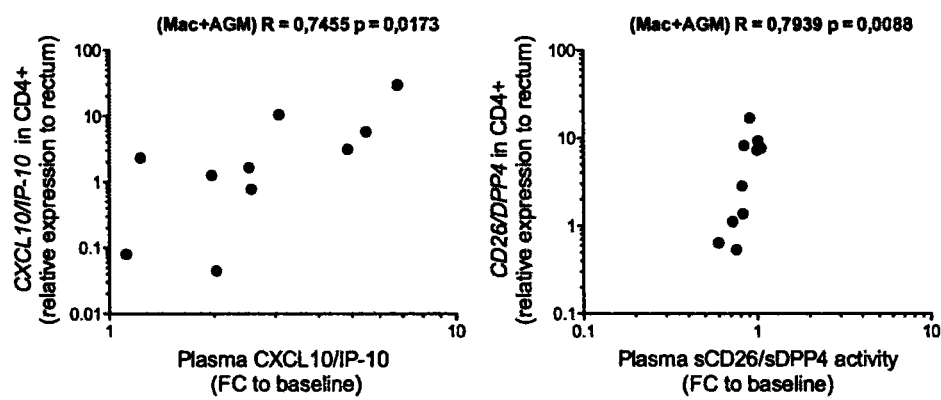
FIG. 6: IP-10 and DPPIV gene expression levels in gut mucosal CD4+ cells correlate with dynamics of IP-10 and DPPIV in the blood of SIV-infected MAC and AGM. Plasma total IP-10 and soluble DPPIV activity were measured as described in previous figure legends at day 65 post-SIV infection of MAC and AGM. Values were normalized against values (median) obtained in plasma samples of the same animals before infection and were expressed as fold change to baseline (FC o baseline). We searched for any correlation between those plasma dynamics with the gene expression levels in the gut mucosal CD4$^+$ compartment. Each individual dot represents paired values for each studied animal.

DPPIV Levels in the Jejunum Correlated with Those in Plasma During SIV Infection The intestine corresponds to the major site of replication for HIV and SIV. According to the literature, virus-host interactions in the intestine have a major impact on the outcome of infection (Douek, *Top HIV Med.*, 15(4): 114-117, 2007). With the help of the animal model, we addressed the question whether the levels of IP-10 and DPPIV in the blood are representative of the respective expression levels in the gut during infection. We quantified IP-10 and soluble DPPIV activity in the plasma of the same animals for which we had analyzed the gut tissues. The activity of soluble DPPIV in the plasma of rapidly progressing macaques seemed lower than in AGM. IP-10 and DPPIV levels in the jejunum correlated with their respective levels in plasma (R=0.77, p=0.03; R=0.79, p=0.009, respectively) (FIG. 6). This is in support for IP-10 and DPPIV in blood as valuable markers reflecting mucosal inflammation in addition to their predictive values for rapid disease progression.

CONCLUSION

Altogether, this is the first time that DPPIV has been measured during acute HIV-1 infection. Our studies in the animal model confirm the link between DPPIV and disease progression. They indicate furthermore that the levels in the blood reflect ongoing pathogenic processes in the tissues.

This is also the first time that the short form of IP-10 has been quantified during HIV infection. In line with the reduced levels of DPPIV, those patients with the worst clinical prognosis, displayed the lowest ratios of short IP-10 as compared to the other HIV-infected individuals.

---

We claim:

1. A method for selecting an anti-HIV therapy for a subject identified as being infected with HIV, said method comprising:
   a) measuring the sIP-10 level in a sample of the said subject by ELISA with an antibody recognizing sIP-10;
   b) measuring the total IP-10 level in said sample of the said subject by ELISA with an antibody recognizina total IP-10;
   c) calculating the ratio of sIP-10 to total IP-10;
   d) determining that said subject has a high likelihood to develop AIDS if the ratio of step c) is less than the ratio of sIP-10 to total IP-10 in a healthy subject;
   e) selecting the therapy based on said likelihood, wherein the therapy is selected from the group consisting of: highly active antiretroviral therapy (HAART), protease inhibitors, fusion inhibitors, integrase inhibitors, co-receptor specific agents, 3TC, AZT, nevirapine, non-nucleoside analogue reverse transcriptase inhibitors, and nucleoside analogue reverse transcriptase inhibitors; and
   f) administering said therapy.

2. The method of claim 1, further comprising a prior step of obtaining said sample.

3. The method of claim 1, wherein said sample is selected from the group of blood, plasma, lymph, bone marrow fluid, pleural fluid, peritoneal fluid, spinal fluid, abdominal fluid, pancreatic fluid, cerebrospinal fluid, brain fluid, ascites, urine, saliva, bronchial lavage, bile, sweat, tear, earflow, sputum, semen, vaginal flow, milk, amniotic fluid, or secretions of respiratory, intestinal or genitourinary tract.

4. The method of claim 1, wherein the subject is selected in the group of subjects havina T cell counts of less than 200 cells/μL, comprised between 200 and 500 cells/μL, and above 500 cells/μL.

5. A method for selecting an anti-WV therapy for a subject identified as being infected with HIV, said method comprising:
   a) measuring the sIP-10 level in a sample of the said subject by ELBA with an antibody recognizing sIP- 10;
   h) measuring the total IP-10 level in said sample of the said subject by ELISA with an antibody recognizing total IP-10;
   c) calculating the ratio of sIP-10 to total IP-10;
   d) determining that the prognosis of said subject is had if the ratio of step c) is less than the ratio of sIP-10 to total IP-10 in a healthy subject; and
   e) selecting the therapy based on said prognosis, wherein wherein the therapy is selected from the group consisting of: highly active antiretroviral therapy (HAART), protease inhibitors, fusion inhibitors, integrase inhibitors, co-receptor specific agents, 3TC, AZT, nevirapine, non-nucleoside analogue reverse transcriptase inhibitors, and nucleoside analogue reverse transcriptase inhibitors; and
   f) administering said therapy.

6. The method of claim 5, further comprising a prior step of obtaining said sample.

7. The method of claim 5, wherein said sample is selected from the group of blood, plasma, lymph, bone marrow fluid, pleural fluid, peritoneal fluid, spinal fluid, abdominal fluid, pancreatic fluid, cerebrospinal fluid, brain fluid, ascites, urine, saliva, bronchial lavage, bile, sweat, tears, ear flow, sputum, semen, vaginal flow, milk, amniotic fluid, or secretions of respiratory, intestinal or genitourinary tract.

8. The method of claim 5, wherein the subject is selected in the group of subjects having T cell counts of less than 200 cells/µL, comprised between 200 and 500 cells/µL, and above 500 cells/µL.

* * * * *